(12) United States Patent
Chen et al.

(10) Patent No.: US 8,258,149 B2
(45) Date of Patent: Sep. 4, 2012

(54) ISOQUINOLINE DERIVATIVES

(75) Inventors: Li Chen, Shanghai (CN); Lichun Feng, Shanghai (CN); Yongguo Li, Shanghai (CN); Guolong Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 117 days.

(21) Appl. No.: 12/770,816

(22) Filed: Apr. 30, 2010

(65) Prior Publication Data

US 2010/0286396 A1 Nov. 11, 2010

(30) Foreign Application Priority Data

May 8, 2009 (WO) ............... PCT/CN2009/071693

(51) Int. Cl.
*A61K 31/47* (2006.01)
*C07D 491/00* (2006.01)
(52) U.S. Cl. ............. 514/280; 546/26; 546/48; 514/277
(58) Field of Classification Search ............... 546/26, 546/42, 48; 514/277, 280
See application file for complete search history.

(56) References Cited

U.S. PATENT DOCUMENTS

| | | | | |
|---|---|---|---|---|
| 6,239,139 | B1 * | 5/2001 | Kim et al. ............ | 514/280 |
| 6,255,317 | B1 * | 7/2001 | Kim et al. ............ | 514/280 |
| 7,517,867 | B2 * | 4/2009 | LaVoie et al. ......... | 514/80 |
| 7,572,809 | B2 * | 8/2009 | Chen et al. ........... | 514/307 |

FOREIGN PATENT DOCUMENTS

| | | |
|---|---|---|
| EP | 2014651 | 1/2009 |
| EP | 2070926 | 6/2009 |
| WO | 2008/040192 | 4/2008 |

OTHER PUBLICATIONS

Leblond et al (2009): STN International HCAPLUS database, (Columbus, Ohio), Accession No. 2009:45500.*
Kim et al (2001): STN International HCAPLUS database, (Columbus, Ohio), Accession No. 2001:480707.*
Moniot et al (1979): STN International HCAPLUS database, (Columbus, Ohio), Accession No. 1979:541060.*
Database Beilstein, Beilstein Institute for Organic Chemistry, Database Accession No. 100092 XP002590163.
Database Beilstein, Beilstein Institute for Organic Chemistry, Database Accession No. 372796 XP002590165.
Moniot, J.L. et al, Journal of Pharmaceutical Sciences, 68:6 (1979) 705-708 XP002590166.
Bastin et al., Organic Process Research & Development, (2000) vol. 4 pp. 427-435.
Ansel et al., Pharm. Dosage Forms & Drug Delivery Systems (1995), pp. 456-457.

* cited by examiner

*Primary Examiner* — Golam M M Shameem
(74) *Attorney, Agent, or Firm* — George W. Johnston; Patricia S. Rocha-Tramaloni; Gene J. Yao

(57) ABSTRACT

The invention provides novel compounds of formula (I)

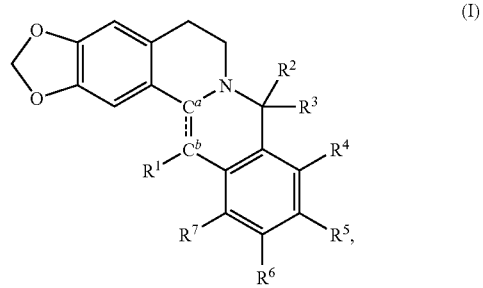

or a pharmaceutically acceptable salt thereof, wherein $R^1$ to $R^7$ are as described herein, compositions including the compounds and methods of preparing and using the compounds.

17 Claims, No Drawings

ISOQUINOLINE DERIVATIVES

PRIORITY TO RELATED APPLICATION(S)

This application claims the benefit of International Pat. Appl. No. PCT/CN2009/071693, filed May 8, 2009, which is hereby incorporated by reference in its entirety.

FIELD OF THE INVENTION

The invention relates to compounds which have glucose uptake activity and are useful in the treatment of diabetes.

Diabetes is a chronic metabolic disorder affecting thousands of millions of people in developed and developing countries. Lack or reduction in insulin secretion due to autoimmune destruction of β-cells is responsible for type 1 diabetes mellitus. The more prevalent form, type 2 diabetes, accounts for more than 90% of cases. The pathogenesis of type 2 diabetes is complex, involving progressive development of insulin resistance and a relative deficiency in insulin secretion, leading to overt hyperglycemia. Both type 1 and type 2 diabetes carry the same risk of debilitating long-term complications, including retinal damage leading to blindness, kidney disease, nerve damage leading to foot amputations, and micro-and macrovascular disease. Since dietary modification and increased physical activity provide insufficient glucose control over the long-term course of the disease, the vast majority of patients require some type of pharmacological intervention.

In response to the enormity of the growing problem, efforts to identify and develop new pharmacological agents for type 2 diabetes have been increasing dramatically in recent years. These efforts have resulted recently in the successful introduction of several new treatment options, and additional new therapies. Currently, there are six classes of oral pharmacological agents available to treat type 2 diabetes including sulfonylureas, meglitinides, metformin (a biguanide), thiazolidinediones and α-glucosidase inhibitors. Sulfonylureas and meglitinides take effect through stimulation of insulin secretion. Metformin can suppress hepatic glucose production; the thiazolidinedione class targets on peripheral tissue insulin resistance; and α-glucosidase inhibitors can inhibit the breakdown of complex carbohydrate in the gut. Sitagliptin (Januvia) is a new class of agents acting as dipeptidyl peptidase IV (DPP-4) inhibitors for the treatment of type 2 diabetes.

It has surprisingly been found that the compounds of the present invention induce a good glucose uptake activity together with a particularly good bioavailability. The compounds of the invention are therefore useful in the treatment of diabetes.

SUMMARY OF THE INVENTION

The invention relates to a compound of formula (I)

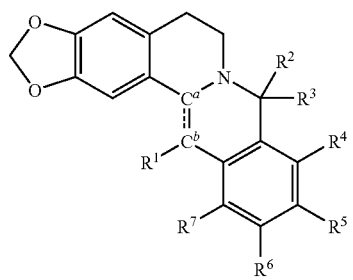

(I)

wherein
$R^1$ is selected from the group consisting of: hydrogen, alkyl, alkenyl, phenylalkyl, pyridinylalkyl, alkylpyrazolylalkyl, carboxyalkyl, alkoxycarbonylalkyl, alkylaminocarbonylalkyl and oxetylaminocarbonylalkyl;
$R^4$ is halogen or alkoxy;
$R^5$ is halogen or alkoxy;
$R^6$ is hydrogen or halogen;
$R^7$ is hydrogen or halogen;
wherein $C^a$ and $C^b$ are each carbon atoms and the bond between $C^a$ and $C^b$ is a single bond or a double bond;
and wherein
a) one of $R^2$ and $R^3$ is hydrogen and the other is selected from phenyl, alkenyl and alkynyl;
b) $R^2$ and $R^3$ are both at the same time alkyl, alkenyl or alkynyl;
c) $R^2$ and $R^3$, together with the carbon atom to which they are attached, form cycloalkyl, cycloalkenyl, oxetyl or tetrahydropyranyl;
or a pharmaceutically acceptable salt thereof;
with the proviso that 9,10-dimethoxy-8,8-dimethyl-5,8-dihydro-6H-[1,3]dioxolo[4,5-g]isoquino[3,2-a]isoquinoline; 8,8-diethyl-9,10-dimethoxy-5,8-dihydro-6H-[1,3]dioxolo[4,5-g]isoquino[3,2-a]isoquinoline; 8,8-diethyl-9,10-dimethoxy-5,8,13,13a-tetrahydro-6H-[1,3]dioxolo[4,5-g]isoquino[3,2-a]isoquinoline; 8-allyl-9,10-dimethoxy-5,8,13,13a-tetrahydro-6H -[1,3]dioxolo[4,5-g]isoquino[3,2-a]isoquinoline; 8-allyl-9,10-dimethoxy-5,8-dihydro-6H-[1,3]dioxolo[4,5-g]isoquino[3,2-a]isoquinoline; 9,10-dimethoxy-8-pent-4-enyl-5,8-dihydro-6H -[1,3]dioxolo[4,5-g]isoquino[3,2-a]isoquinoline; 9,10-dimethoxy-8-phenyl-5,8-dihydro-6H-[1,3]dioxolo[4,5-g]isoquino[3,2-a]isoquinoline; and 9,10-dimethoxy-8,8-dimethyl-5,8,13,13a-tetrahydro-6H-[1,3]dioxolo[4,5-g]isoquino[3,2-a]isoquinoline are excluded.

The invention also relates to a process for the manufacture of these novel compounds and medicaments containing them. The compounds of the invention have glucose uptake activity, which results in lowered blood glucose. The invention thus also concerns the use of such compounds for the treatment of metabolic diseases such as hyperglycemia and type 2 diabetes and for the manufacture of corresponding medicaments.

DETAILED DESCRIPTION OF THE INVENTION

Definitions

As used herein, the term "alkyl" alone or in combination signifies a saturated, linear-or branched chain alkyl group containing 1 to 8, preferably 1 to 6, more preferably 1 to 4 carbon atoms, for example methyl, ethyl, propyl, isopropyl, 1-butyl, 2-butyl, tert-butyl and the like. Preferred "alkyl" groups are methyl and ethyl.

The term "alkoxy" alone or in combination signifies a group alkyl-O—, wherein the "alkyl" is as defined above; for example methoxy, ethoxy, propoxy, isopropoxy, n-butoxy, i-butoxy, 2-butoxy, t-butoxy and the like. Preferred alkoxy groups are methoxy and ethoxy and more preferably methoxy.

The term "alkenyl" alone or in combination signifies an alkyl group as defined above wherein one or more carbon-carbon single bond is replaced by a carbon-carbon double bond. Examples of alkenyl are ethenyl, propenyl, n-butenyl, i-butenyl and the like. Preferred alkenyl groups are ethenyl, propenyl and i-propenyl.

The term "cycloalkyl" alone or in combination refers to a saturated carbon ring containing from 3 to 7 carbon atoms, preferably from 3 to 6 carbon atoms, for example, cyclopropyl, cyclobutyl, cyclopentyl, cyclohexyl, cycloheptyl and the like. A preferred cycloalkyl group is cyclopentyl.

The term "cycloalkenyl" alone or in combination refers to a cycloalkyl group as defined above wherein one or more carbon-carbon single bond is replaced by a carbon-carbon double bond. Examples of cycloalkenyl are cyclopentenyl, cyclohexenyl and cycloheptenyl. Preferred cycloalkenyl group is cyclopentenyl.

The term "alkynyl" alone or in combination signifies an alkyl group as defined above wherein one or more carbon-carbon single bond is replaced by a carbon-carbon triple bond. Examples of alkynyl are ethynyl, propynyl, n-butynyl, i-butynyl, and the like. Preferred alkynyl groups are ethynyl and propynyl.

The term "halogen" means fluorine, chlorine, bromine or iodine. Halogen is preferably chlorine.

The term "carboxy" alone or in combination refers to the group —COOH.

The term "carbonyl" alone or in combination refers to the group —C(O)—.

The term "amino" alone or in combination refers to primary, secondary or tertiary amino.

Compounds of the Present Invention

The invention relates to a compound of formula (I)

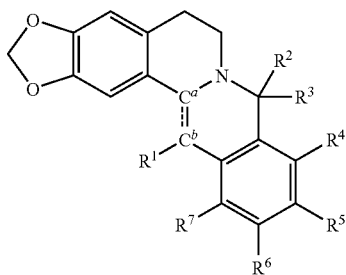

(I)

wherein
$R^1$ is selected from the group consisting of: hydrogen, alkyl, alkenyl, phenylalkyl, pyridinylalkyl, alkylpyrazolylalkyl, carboxyalkyl, alkoxycarbonylalkyl, alkylaminocarbonylalkyl and oxetylaminocarbonylalkyl;
$R^4$ is halogen or alkoxy;
$R^5$ is halogen or alkoxy;
$R^6$ is hydrogen or halogen;
$R^7$ is hydrogen or halogen;
wherein $C^a$ and $C^b$ are each carbon atoms and the bond between $C^a$ and $C^b$ is a single bond or a double bond;
and wherein
a) one of $R^2$ and $R^3$ is hydrogen and the other is selected from phenyl, alkenyl and alkynyl;
b) $R^2$ and $R^3$ are both at the same time alkyl, alkenyl or alkynyl;
c) $R^2$ and $R^3$, together with the carbon atom to which they are attached, form cycloalkyl, cycloalkenyl, oxetyl or tetrahydropyranyl;
or a pharmaceutically acceptable salt thereof;
with the proviso that 9,10-dimethoxy-8,8-dimethyl-5,8-dihydro-6H-[1,3]dioxolo[4,5-g]isoquino[3,2-a]isoquinoline; 8,8-diethyl-9,10-dimethoxy-5,8-dihydro-6H-[1,3]dioxolo[4,5-g]isoquino[3,2-a]isoquinoline; 8,8-diethyl-9,10-dimethoxy-5,8,13,13a-tetrahydro-6H-[1,3]dioxolo[4,5-g]isoquino[3,2-a]isoquinoline; 8-allyl-9,10-dimethoxy-5,8,13,13a-tetrahydro-6H-[1,3]dioxolo[4,5-g]isoquino[3,2-a]isoquinoline; 8-allyl-9,10-dimethoxy-5,8-dihydro-6H-[1,3]dioxolo[4,5-g]isoquino[3,2-a]isoquinoline; 9,10-dimethoxy-8-pent-4-enyl-5,8-dihydro-6H-[1,3]dioxolo[4,5-g]isoquino[3,2-a]isoquinoline; 9,10-dimethoxy-8-phenyl-5,8-dihydro-6H-[1,3]dioxolo[4,5-g]isoquino[3,2-a]isoquinoline; and 9,10-dimethoxy-8,8-dimethyl-5,8,13,13a-tetrahydro-6H-[1,3]dioxolo[4,5-g]isoquino[3,2-a]isoquinoline are excluded.

Compounds of the general formula (I) which contain one or several chiral centers can either be present as racemates, diastereomeric mixtures, or optically active single isomers. The racemates can be separated according to known methods into the enantiomers. Preferably, diastereomeric salts which can be separated by crystallization are formed from the racemic mixtures by reaction with an optically active acid such as e.g. D-or L-tartaric acid, mandelic acid, malic acid, lactic acid or camphorsulfonic acid.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457.

Particularly preferred is a compound of formula (I) wherein $R^1$ is selected from the group consisting of: hydrogen, alkyl, phenylalkyl, pyridinylalkyl and alkenyl.

Further preferred is a compound of formula (I) wherein $R^1$ is selected from the group consisting of: hydrogen, methyl, ethyl, propenyl, benzyl, pyridinylmethyl, 1-methyl-1H-pyrazolylmethyl, carboxymethyl, methoxycarbonylmethyl, propylaminocarbonylmethyl, dimethylaminocarbonylmethyl and oxetylaminocarbonylmethyl.

Particularly preferred is a compound of formula (I) wherein $R^1$ is selected from the group consisting of: hydrogen, methyl, ethyl, propenyl, benzyl and pyridinylmethyl. Also preferred is a compound of formula (I) wherein $R^1$ is selected from the group consisting of: hydrogen, methyl and ethyl.

Preferred is a compound of formula (I) wherein one of $R^2$ and $R^3$ is hydrogen and the other is selected from the group consisting of: phenyl, alkenyl and alkynyl. Further preferred is a compound of formula (I) wherein $R^2$ and $R^3$ are both at the same time alkyl, alkenyl or alkynyl. A compound of formula (I) wherein $R^2$ and $R^3$, together with the carbon atom to which they are attached, form cycloalkyl, cycloalkenyl, oxetyl or tetrahydropyranyl is also preferred.

A compound of formula (I) wherein one of $R^2$ and $R^3$ is hydrogen and the other is selected from alkenyl and alkynyl is preferred. Furthermore, preferred is a compound of formula (I) wherein one of $R^2$ and $R^3$ is hydrogen and the other one is selected from the group consisting of: phenyl, ethenyl, propenyl, ethynyl and propynyl.

iso-propenyl is a preferred propenyl. n-propenyl is another preferred propenyl.

Further preferred is a compound of formula (I) wherein one of $R^2$ and $R^3$ is hydrogen and the other is selected from the group consisting of: ethenyl, propenyl, ethynyl and propynyl. Moreover, a compound of formula (I) wherein one of $R^2$ and $R^3$ is hydrogen and the other one is selected from the group consisting of propenyl, ethynyl and propynyl is further preferred.

A compound of formula (I) wherein $R^2$ and $R^3$ are identical is preferred.

A compound of formula (I) wherein $R^2$ and $R^3$ are identical and are both at the same time alkyl, alkenyl or alkynyl is preferred.

Preferred is a compound of formula (I) wherein in $R^2$ and $R^3$ are both at the same time methyl, ethyl or propenyl.

Moreover, preferred is a compound of formula (I) wherein in $R^2$ and $R^3$, together with the carbon atom to which they are attached, form cycloalkyl or cycloalkenyl.

Furthermore, a compound of formula (I) wherein $R^2$ and $R^3$, together with the carbon atom to which they are attached, form cyclopentyl or cyclopentenyl is preferred.

Preferred is a compound of formula (I) wherein $R^4$ is alkoxy and in particular methoxy.

Also preferred is a compound of formula (I) wherein $R^5$ is alkoxy and in particular methoxy.

Further preferred is a compound of formula (I) wherein $R^6$ is hydrogen or chloro. $R^6$ is preferably hydrogen.

Particularly preferred is a compound of formula (I) wherein $R^7$ is hydrogen or chloro. $R^7$ is preferably hydrogen.

Particularly preferred compounds of formula (I) are selected from the group consisting of:

9,10-Dimethoxy-8-vinyl-5,8-dihydro-6H-[1,3]dioxolo[4,5-g]isoquino[3,2-a]isoquinoline;

9',10'-Dimethoxy-5',6',13',13a'-tetrahydrospiro[cyclopentane-1,8'-[1,3]dioxolo[4,5-g]isoquino[3,2-a]isoquinoline];

8-Isopropenyl-9,10-dimethoxy-5,8-dihydro-6H-[1,3]dioxolo[4,5-g]isoquino[3,2-a]isoquinoline;

8-Ethynyl-9,10-dimethoxy-5,8-dihydro-6H-[1,3]dioxolo[4,5-g]isoquino[3,2-a]isoquinoline;

9,10-Dimethoxy-8-prop-1-ynyl-5,8-dihydro-6H-[1,3]dioxolo[4,5-g]isoquino[3,2-a]isoquinoline;

8-Isopropenyl-9,10-dimethoxy-13-methyl-5,8-dihydro-6H-[1,3]dioxolo[4,5-g]isoquino[3,2-a]isoquinoline;

9,10-Dimethoxy-13-methyl-8-prop-1-ynyl-5,8-dihydro-6H-[1,3]dioxolo[4,5-g]isoquino[3,2-a]isoquinoline;

13-Ethyl-8-isopropenyl-9,10-dimethoxy-5,8-dihydro-6H-[1,3]dioxolo[4,5-g]isoquino[3,2-a]isoquinoline;

8-Allyl-13-ethyl-9,10-dimethoxy-5,8-dihydro-6H-[1,3]dioxolo[4,5-g]isoquino[3,2-a]isoquinoline;

13-Ethyl-9,10-dimethoxy-8-prop-1-ynyl-5,8-dihydro-6H-[1,3]dioxolo[4,5-g]isoquino[3,2-a]isoquinoline;

13-Allyl-8-isopropenyl-9,10-dimethoxy-5,8-dihydro-6H-[1,3]dioxolo[4,5-g]isoquino[3,2-a]isoquinoline;

9,10-Dimethoxy-8,8,13-trimethyl-5,8-dihydro-6H-[1,3]dioxolo[4,5-g]isoquino[3,2-a]isoquinoline;

8,8-Diethyl-9,10-dimethoxy-13-methyl-5,8-dihydro-6H-[1,3]dioxolo[4,5-g]isoquino[3,2-a]isoquinoline;

13-Ethyl-9,10-dimethoxy-8,8-dimethyl-5,8-dihydro-6H-[1,3]dioxolo[4,5-g]isoquino[3,2-a]isoquinoline;

8,8-Diallyl-9,10-dimethoxy-5,8-dihydro-6H-[1,3]dioxolo[4,5-g]isoquino[3,2-a]isoquinoline;

13-Benzyl-9,10-dimethoxy-8,8-dimethyl-5,8-dihydro-6H-[1,3]dioxolo[4,5-g]isoquino[3,2-a]isoquinoline;

12-Chloro-9,10-dimethoxy-8,8-dimethyl-5,8-dihydro-6H-[1,3]dioxolo[4,5-g]isoquino[3,2-a]isoquinoline;

9',10'-Dimethoxy-5',6'-dihydrospiro[cyclopentane-1,8'-[1,3]dioxolo[4,5-g]isoquino[3,2-a]isoquinoline];

9,10-Dimethoxy-8,8,13-trimethyl-5,8,13,13a-tetrahydro-6H-[1,3]dioxolo[4,5-g]isoquino[3,2-a]isoquinoline;

8,8-Diethyl-9,10-dimethoxy-13-methyl-5,8,13,13a-tetrahydro-6H-[1,3]dioxolo[4,5-g]isoquino[3,2-a]isoquinoline;

9,10-Dimethoxy-8,8-dimethyl-13-pyridin-2-ylmethyl-5,8,13,13a-tetrahydro-6H-[1,3]dioxolo[4,5-g]isoquino[3,2-a]isoquinoline;

13-Benzyl-9,10-dimethoxy-8,8-dimethyl-5,8,13,13a-tetrahydro-6H-[1,3]dioxolo[4,5-g]isoquino[3,2-a]isoquinoline; and 9',10'-Dimethoxy-5',6',13',13a'-tetrahydrospiro[cyclopent-3-ene-1,8'-[1,3]dioxolo[4,5-g]isoquino[3,2-a]isoquinoline].

The following compounds of formula (I) are particularly preferred:

9',10'-Dimethoxy-5',6',13',13a'-tetrahydrospiro[cyclopentane-1,8'-[1,3]dioxolo[4,5-g]isoquino[3,2-a]isoquinoline];

8-Isopropenyl-9,10-dimethoxy-5,8-dihydro-6H-[1,3]dioxolo[4,5-g]isoquino[3,2-a]isoquinoline;

8-Ethynyl-9,10-dimethoxy-5,8-dihydro-6H-[1,3]dioxolo[4,5-g]isoquino[3,2-a]isoquinoline;

9,10-Dimethoxy-8-prop-1-ynyl-5,8-dihydro-6H-[1,3]dioxolo[4,5-g]isoquino[3,2-a]isoquinoline;

8-Isopropenyl-9,10-dimethoxy-13-methyl-5,8-dihydro-6H-[1,3]dioxolo[4,5-g]isoquino[3,2-a]isoquinoline;

9,10-Dimethoxy-13-methyl-8-prop-1-ynyl-5,8-dihydro-6H-[1,3]dioxolo[4,5-g]isoquino[3,2-a]isoquinoline;

13-Ethyl-9,10-dimethoxy-8-prop-1-ynyl-5,8-dihydro-6H-[1,3]dioxolo[4,5-g]isoquino[3,2-a]isoquinoline;

9,10-Dimethoxy-8,8,13-trimethyl-5,8-dihydro-6H-[1,3]dioxolo[4,5-g]isoquino[3,2-a]isoquinoline;

12-Chloro-9,10-dimethoxy-8,8-dimethyl-5,8-dihydro-6H-[1,3]dioxolo[4,5-g]isoquino[3,2-a]isoquinoline;

9',10'-Dimethoxy-5',6'-dihydrospiro[cyclopentane-1,8'-[1,3]dioxolo[4,5-g]isoquino[3,2-a]isoquinoline];

9,10-Dimethoxy-8,8,13-trimethyl-5,8,13,13a-tetrahydro-6H-[1,3]dioxolo[4,5-g]isoquino[3,2-a]isoquinoline; and 9',10'-Dimethoxy-5',6',13',13a'-tetrahydrospiro[cyclopent-3-ene-1,8'-[1,3]dioxolo[4,5-g]isoquino[3,2-a]isoquinoline].

The compounds of the present invention can be prepared according to the following procedures.

In the following schemes R refers to phenyl, alkyl, alkenyl or alkynyl. $R^1$ to $R^7$ are as defined above unless otherwise indicated.

Synthesis

A. General Synthetic Route for 8-Monosubstituted Analogues Ia (Scheme 1)

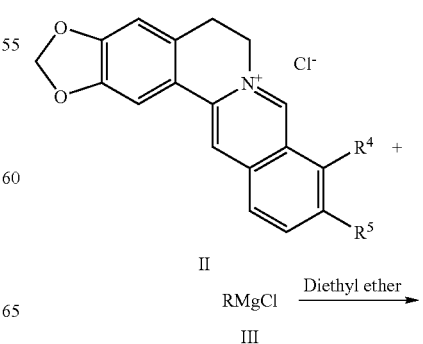

Scheme 1

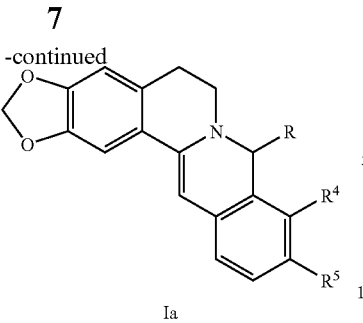

Compounds Ia can be prepared according to Scheme 1. Starting with II, Grignard reaction with different Grignard reagents III gives Ia. The reaction is typically carried out in etheral solvents.

B. General Synthetic Route for 8,13-Disubstituted Analogues Ib (Scheme 2)

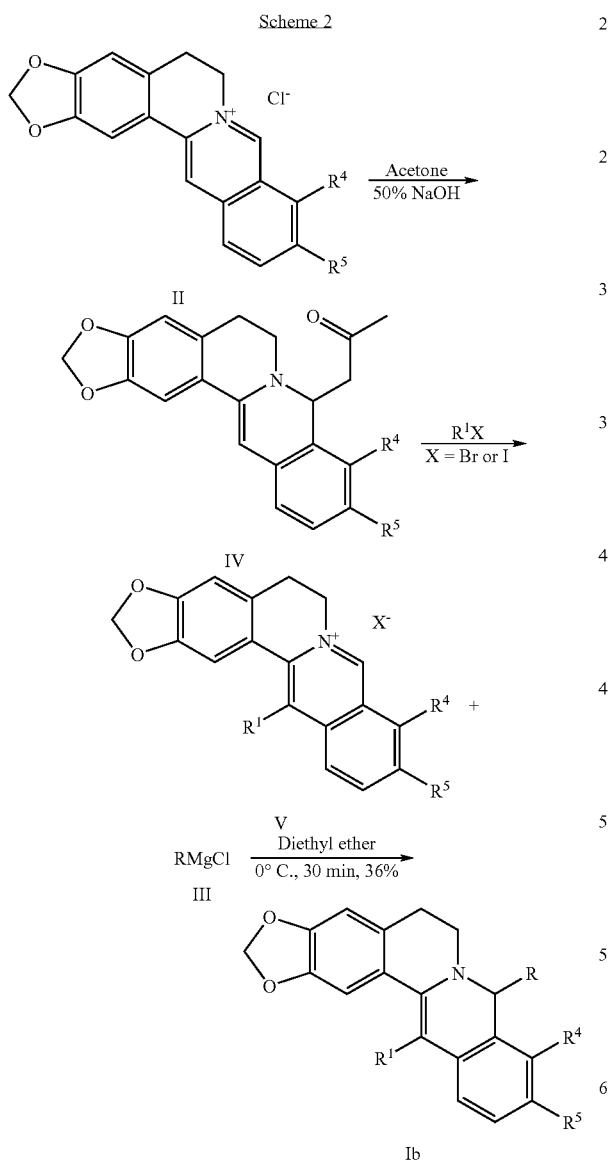

Compounds Ib can be prepared according to Scheme 2. Starting with II, treatment with 50% aqueous sodium hydroxide in the presence of acetone affords IV. Treatment of IV with different halides provides 13-sustituted berberine analogs V. The reaction is carried out uder neat condition. Further treatment of V with various Grignard reagents affords Ib.

C. General Synthetic Route for 8-Gem-Disubstituted Analogues Ic (Scheme 3)

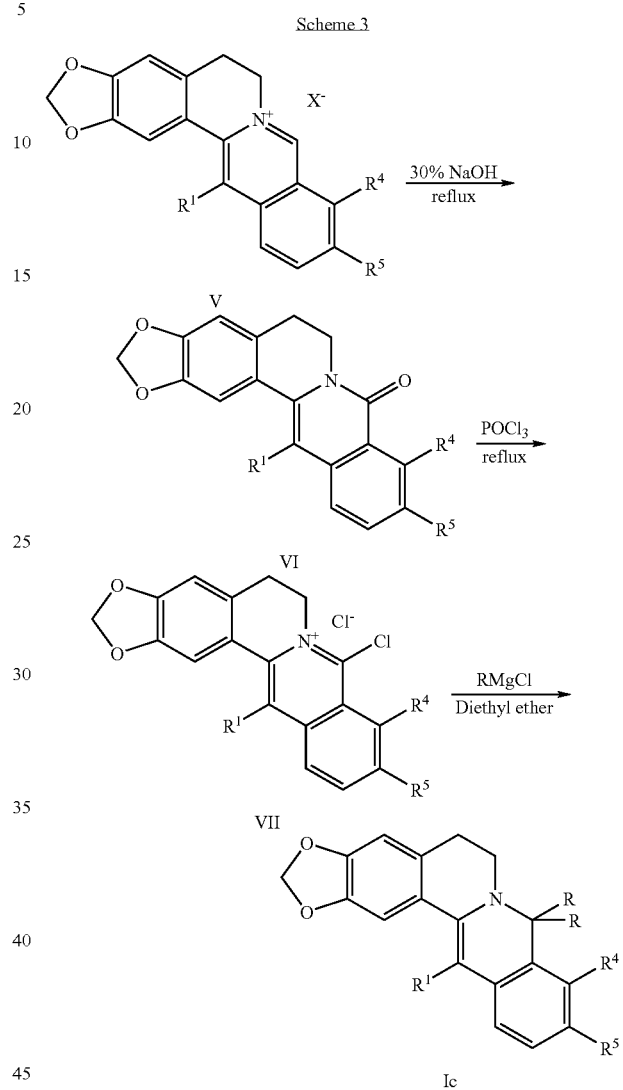

Compounds Ic can be prepared according to Scheme 3. Starting with V, treatment with 30% aqueous sodium hydroxide under reflux condition affords VI. Treatment of VI with phosphorus(III) oxychloride provides VII which is further reacted with various Grignard reagents to afford Ic.

D. General Synthetic Route for Halogen-Substituted Analogues Id (Scheme 4)

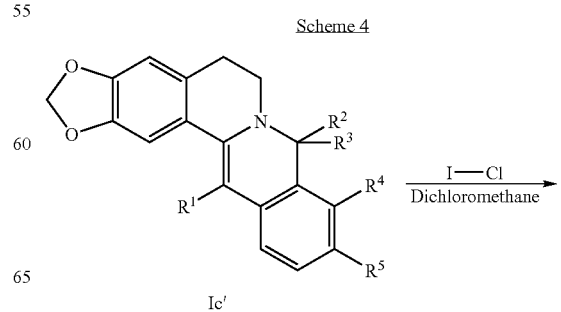

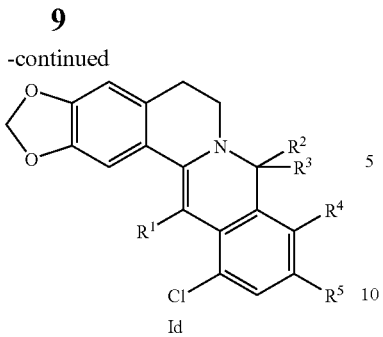

Id

Compounds Id can be prepared according to Scheme 4. Starting with 13-substituted 8-disubstituted berberine analogs Ic', treatment with Iodine monochloride in the presence of dichloromethane affords Id.

E. General Synthetic Route for 8-Spiro Analogues Ie (Scheme 5)

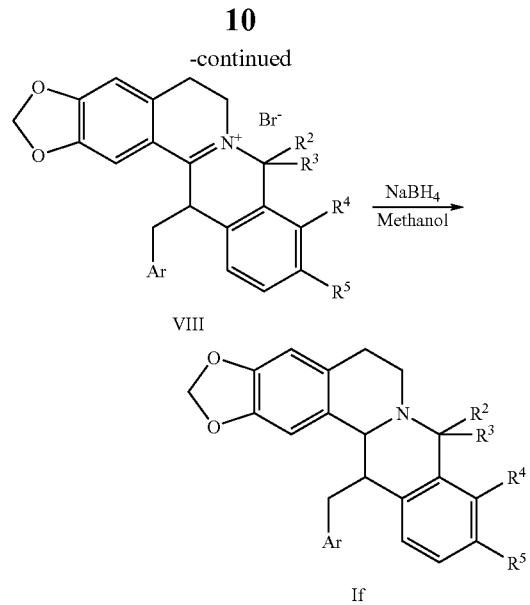

Compounds Ie can be prepared according to Scheme 5. Starting with VII, treatment with bis-Grignard reagent derived from 1,4-dibromobutane in tetrahydrofuran affords spiro compound Ie.

F. General Synthetic Route for Tetrahydro Berberine Analogues If and Ig (Scheme 6)

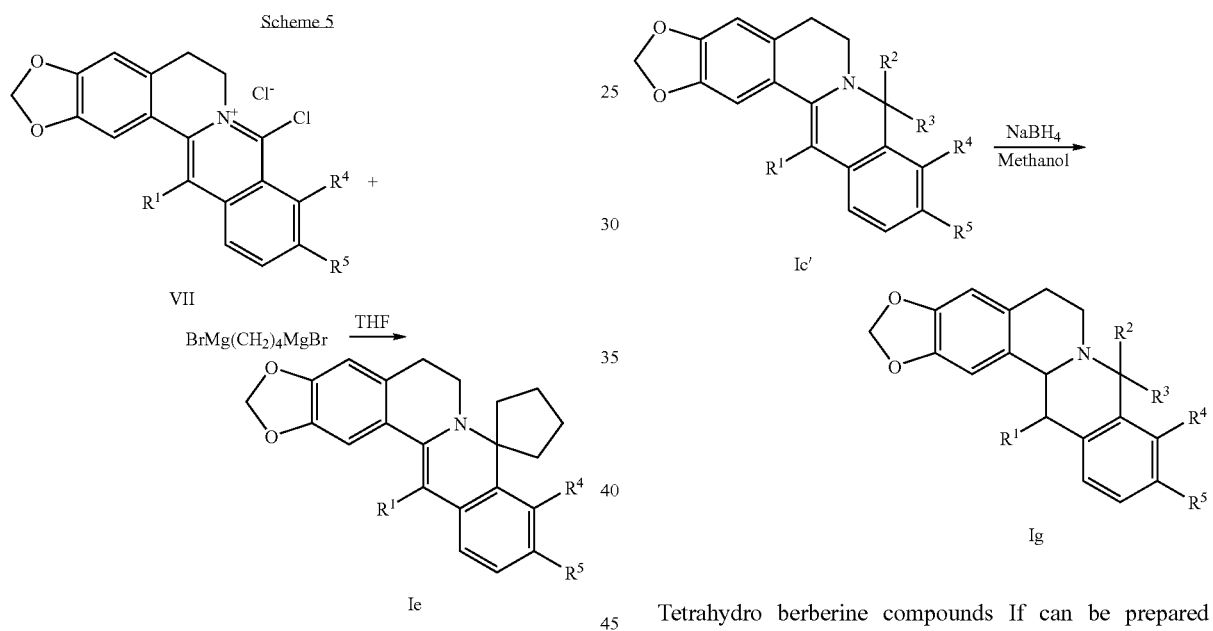

Tetrahydro berberine compounds If can be prepared according to Scheme 6. Starting with Ic', treatment with various bromides in the presence of chloroform affords iminium salts VIII. Further treatment with sodium boronhydride in the presence of methanol affords If. Direct reduction of Ic with sodium borohydride in the presence of methanol affords Ig.

G. General Synthetic Route for Spiro Tetrahydro Berberine Analogues Ih and Ii (Scheme 7)

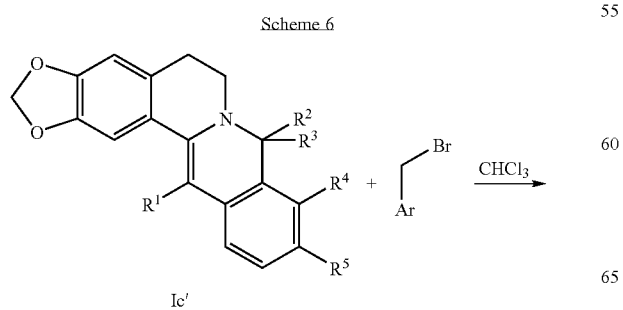

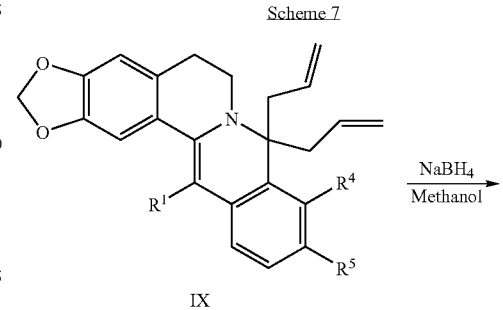

-continued

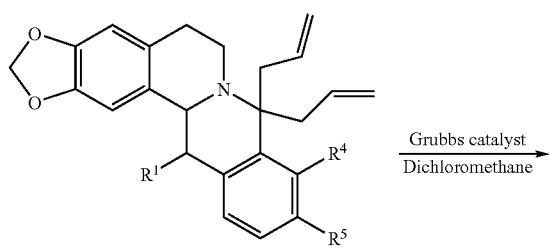
X

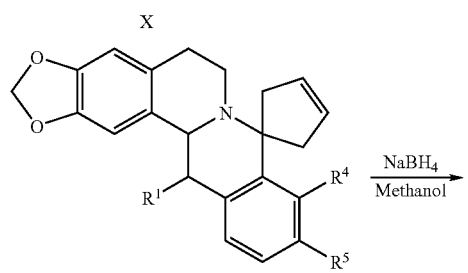
Ih

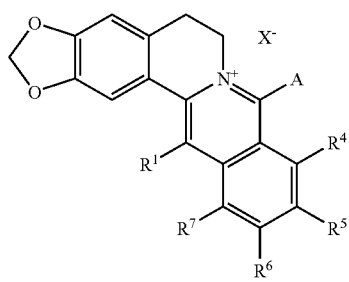
Ii

Compounds Ih can be prepared according to Scheme 7. Starting with 8-disubstituted analogs IX, treatment with sodium boronhydride in the presence of methanol affords tetrahydro analog X.

Further treatment of X with Grubb's catalyst in the presence of dichloromethane gives Ih. 8-disubstituted analogs IX can be prepared according to Scheme 3.

Compounds Ii can be prepared starting with 8-disubstituted analogs Ih. Reduction of Ih with sodium boronhydride in the presence of methanol affords Ii.

The invention also relates to a process for the preparation of a compound of formula (I) comprising one of the following steps:

(a) the reaction of a compound according to formula (A)

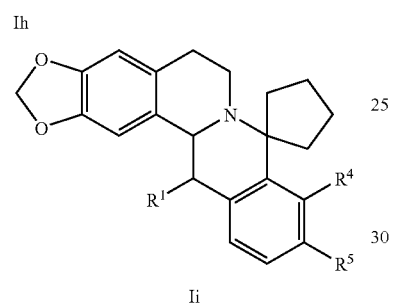
(A)

in the presence of RMgY or in the presence of YMg(CH$_2$)$_4$MgY;

(b) the reaction of a compound according to formula (B)

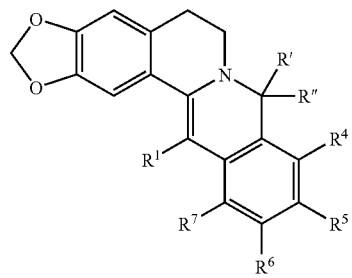
(B)

in the presence of I—Cl;

(c) the reaction of a compound according to formula (C)

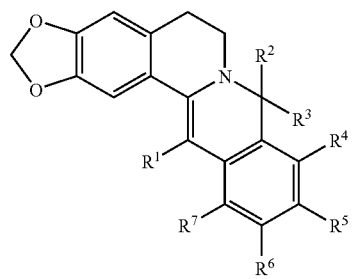
(C)

in the presence of NaBH$_4$; or (d) the reaction of a compound according to formula (D)

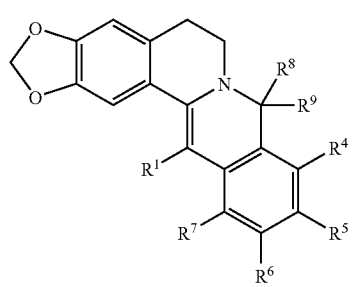
(D)

in the presence of a Grubbs catalyst;

wherein R$^1$ to R$^7$ are as defined above, R$^8$ and R$^9$ are alkenyl, A is hydrogen or Cl, R is selected from alkyl, alkenyl, alkynyl and phenyl, R' and R" are selected from alkyl, alkenyl and alkynyl, and X and Y are selected from Cl and Br.

The reaction of step (a) is preferably carried out in ethereal solvent, preferably in diethyl ether or THF. The reaction temperature is preferably between 0° C. and 25° C.

The reactions of step (b) and (c) are preferably carried out in methanol. The reaction of step (d) is preferably carried out in dichloromethane.

Grubbs catalyst refers to a catalyst suitable for olefin metathesis, e.g. the first generation Grubbs catalyst, e.g. benzylidene-bis(tricyclohexylphosphine)dichloro ruthenium.

Pharamceutical Compositions and Administration

The invention also relates to a pharmaceutical composition comprising a compound of formula (I)

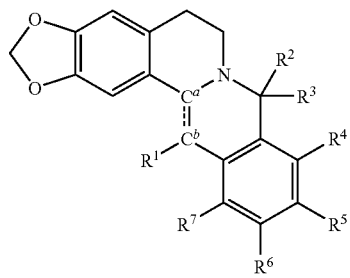

wherein
$R^1$ is selected from the group consisting of: hydrogen, alkyl, alkenyl, phenylalkyl, pyridinylalkyl, alkylpyrazolylalkyl, carboxyalkyl, alkoxycarbonylalkyl, alkylaminocarbonylalkyl and oxetylaminocarbonylalkyl;
$R^4$ is halogen or alkoxy;
$R^5$ is halogen or alkoxy;
$R^6$ is hydrogen or halogen;
$R^7$ is hydrogen or halogen;
wherein $C^a$ and $C^b$ are each carbon atoms and the bond between $C^a$ and $C^b$ is a single bond or a double bond;
and wherein
a) one of $R^2$ and $R^3$ is hydrogen and the other is selected from phenyl, alkenyl and alkynyl;
b) $R^2$ and $R^3$ are both at the same time alkyl, alkenyl or alkynyl;
c) $R^2$ and $R^3$, together with the carbon atom to which they are attached, form cycloalkyl, cycloalkenyl, oxetyl or tetrahydropyranyl;
or a pharmaceutically acceptable salt thereof.

The use of a compound of formula (I)

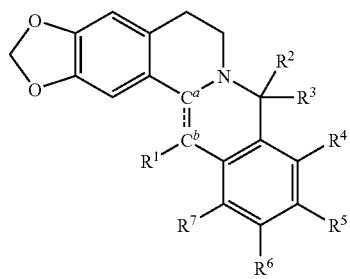

wherein
$R^1$ is selected from the group consisting of: hydrogen, alkyl, alkenyl, phenylalkyl, pyridinylalkyl, alkylpyrazolylalkyl, carboxyalkyl, alkoxycarbonylalkyl, alkylaminocarbonylalkyl and oxetylaminocarbonylalkyl;
$R^4$ is halogen or alkoxy;
$R^5$ is halogen or alkoxy;
$R^6$ is hydrogen or halogen;
$R^7$ is hydrogen or halogen;
wherein $C^a$ and $C^b$ are each carbon atoms and the bond between $C^a$ and $C^b$ is a single bond or a double bond;
and wherein
a) one of $R^2$ and $R^3$ is hydrogen and the other is selected from phenyl, alkenyl and alkynyl;
b) $R^2$ and $R^3$ are both at the same time alkyl, alkenyl or alkynyl;
c) $R^2$ and $R^3$, together with the carbon atom to which they are attached, form cycloalkyl, cycloalkenyl, oxetyl or tetrahydropyranyl;
or a pharmaceutically acceptable salt thereof;
for the preparation of medicaments for the treatment or prophylaxis of hyperglycemia or type 2 diabetes is also an object of the invention.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

A compound of formula (I) when manufactured according to the above process is also an object of the invention.

Furthermore, the invention also relates to a method for the treatment or prophylaxis of hyperglycemia or type 2 diabetes, which method comprises administering an effective amount of a compound of formula (I)

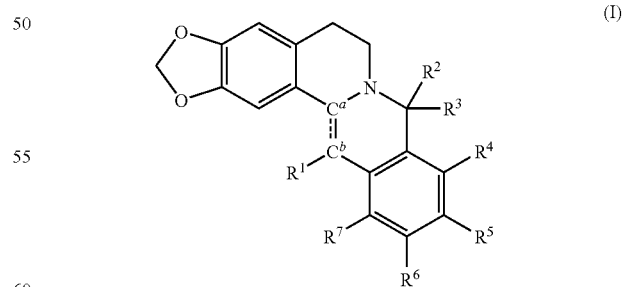

wherein
$R^1$ is selected from the group consisting of: hydrogen, alkyl, alkenyl, phenylalkyl, pyridinylalkyl, alkylpyrazolylalkyl, carboxyalkyl, alkoxycarbonylalkyl, alkylaminocarbonylalkyl and oxetylaminocarbonylalkyl;
$R^4$ is halogen or alkoxy;
$R^5$ is halogen or alkoxy;

$R^6$ is hydrogen or halogen;
$R^7$ is hydrogen or halogen;
wherein $C^a$ and $C^b$ are each carbon atoms and the bond between $C^a$ and $C^b$ is a single bond or a double bond;
and wherein
a) one of $R^2$ and $R^3$ is hydrogen and the other is selected from phenyl, alkenyl and alkynyl;
b) $R^2$ and $R^3$ are both at the same time alkyl, alkenyl or alkynyl;
c) $R^2$ and $R^3$, together with the carbon atom to which they are attached, form cycloalkyl, cycloalkenyl, oxetyl or tetrahydropyranyl;
or a pharmaceutically acceptable salt thereof.

EXAMPLES

The invention is illustrated by the following examples which have no limiting character. Unless explicitly otherwise stated, all reactions, reaction conditions, abbreviations and symbols have the meanings well known to a person of ordinary skill in organic chemistry.

Abbreviations used herein are as follows:
BSA: bovine serum albumin;
calcd: calculated;
DCM: dichloromethane;
DMEM: Dulbecco's Modified Eagle Medium;
DMSO: dimethylsulfoxide;
FBS: fetal bovine serum;
h: hour or hours;
MHz: megahertz;
min: minute or minutes;
mL: milliliter;
mmol: millimole;
PBS: phosphate buffer solution.

Example 1

9,10-Dimethoxy-8-phenyl-5,8-dihydro-6H-[1,3]dioxolo[4,5-g]isoquino[3,2-a]isoquinoline

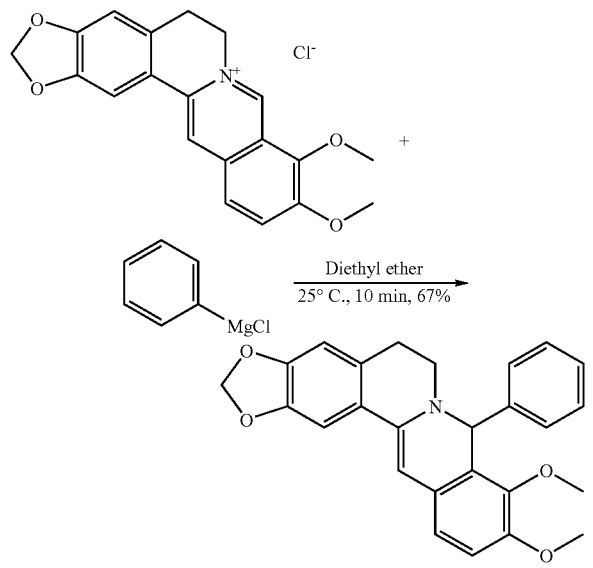

To a suspension of berberine hydrochloride (400 mg, 1.08 mmol) in anhydrous diethyl ether (50 mL) at 0° C. was added phenylmagnesium chloride solution (2.8 mL, 2.7 mmol) dropwise. After stirring at 0° C. for 10 min, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 9,10-dimethoxy-8-phenyl-5,8-dihydro-6H-[1,3]dioxolo[4,5-g]isoquino[3,2-a]isoquinoline (300 mg, 67%). LC/MS m/e calcd for $C_{26}H_{23}NO_4$ (M+H)$^+$: 414.48, observed: 414.2; 1H NMR (400 MHz, DMSO-d6) δ ppm 2.67-2.90 (m, 3 H) 3.35-3.41 (m, 1 H) 3.49 (s, 3 H) 3.74 (s, 3 H) 5.70 (s, 1 H) 5.99 (d, J=1.52 Hz, 2 H) 5.98 (s, 1 H) 6.72 (s, 1 H) 6.80 (m, 1 H) 6.88 (m, 1 H) 7.16-7.28 (m, 4 H) 7.35 (d, J=7.07 Hz, 2 H).

Example 2

9',10'-Dimethoxy-5',6',13',13a'-tetrahydrospiro[cyclopentane-1,8'-[1,3]dioxolo[4,5-g]isoquino[3,2-a]isoquinoline]

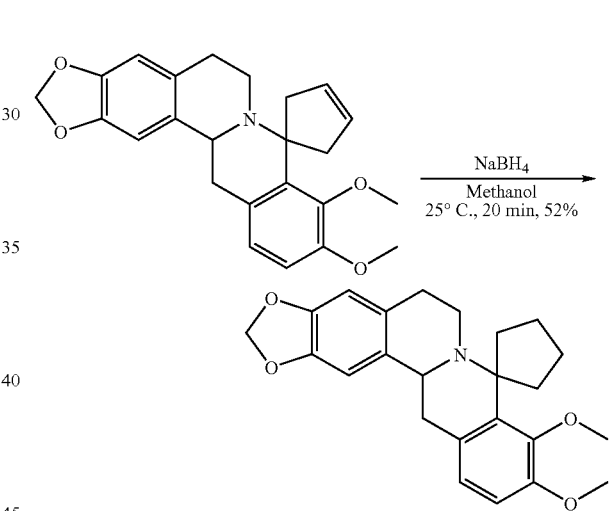

To a solution of 9',10'-dimethoxy-5',6',13',13a'-tetrahydrospiro[cyclopent-3-ene-1,8'-[1,3]dioxolo[4,5-g]isoquino[3,2-a]isoquinoline] (300 mg, 0.75 mmol) in methanol (20 mL) was added sodium borohydride (57 mg, 1.5 mmol) in small portions at 25° C. After stirring at 25° C. for 2 h, the reaction solvent was concentrated in vacuo. The resulting residue was extracted with diethyl ether (2×50 mL), washed with water (2×25 mL), dried over anhydrous sodium sulfate and concentrated in vacuo to afford 9',10'-dimethoxy-5',6',13',13a'-tetrahydrospiro [cyclopentane-1,8'-[1,3]dioxolo[4,5-g]isoquino[3,2-a]isoquinoline] (155 mg, 52%). LC/MS m/e calcd for $C_{24}H_{27}NO_4$ (M+H)$^+$: 394.49, observed: 394.3; 1H NMR (400 MHz, DMSO-d6) δ ppm 1.64-1.80 (m, 2 H) 1.85-1.96 (m, 2 H) 1.96-2.08 (m, 2 H) 2.16-2.25 (m, 1 H) 2.25-2.35 (m, 1 H) 2.56-2.65 (m, 2 H) 2.65-2.71 (m, 2 H) 2.93-3.03 (m, 2 H) 3.78 (d, J=6.57 Hz, 6 H) 3.91 (d, J=7.83 Hz, 1 H) 5.94 (d, J=3.54 Hz, 2 H) 6.65 (s, 1 H) 6.73 (d, J=8.34 Hz, 1 H) 6.84 (s, 1 H) 6.88 (d, J=8.34 Hz, 1 H).

Example 3

9,10-Dimethoxy-8-vinyl-5,8-dihydro-6H-[1,3]dioxolo[4,5-g]isoquino[3,2-a]isoquinoline

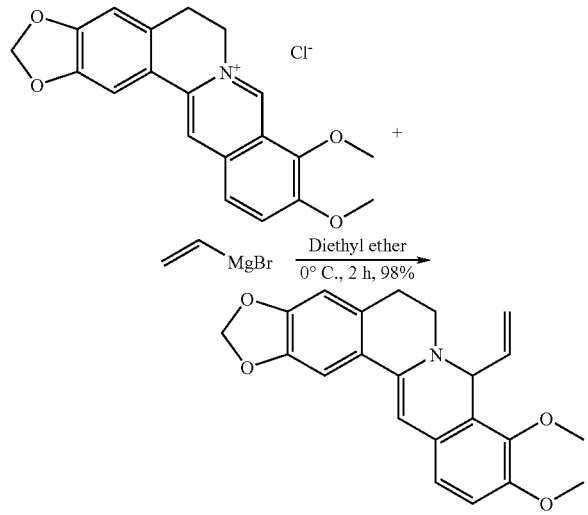

To a suspension of berberine hydrochloride (500 mg, 1.3 mmol) in anhydrous diethyl ether (100 mL) at 0° C. was added vinylmagnesium bromide solution (1.0 M in tetrahydrofuran, 13 mL, 13 mmol) dropwise. After stirring at 0° C. for 2 h, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 9,10-dimethoxy-8-vinyl-5,8-dihydro-6H-[1,3]dioxolo[4,5-g]isoquino[3,2-a]isoquinoline (480 mg, 98%). LC/MS m/e calcd for $C_{22}H_{21}NO_4$ $(M+H)^+$: 364.32, observed: 364.1; 1H NMR (400 MHz, DMSO-d6) δ ppm 2.74-2.84 (m, 2 H) 3.16-3.24 (m, 2 H) 3.75 (s, 3 H) 3.77 (s, 3 H) 4.97 (d, J=10.11 Hz, 1 H) 5.06 (dd, J=4.55, 2.53 Hz, 2 H) 5.85-5.93 (m, 1 H) 5.95 (s, 1 H) 6.00 (d, J=5.31 Hz, 2 H) 6.72 (d, J=8.34 Hz, 1 H) 6.77 (s, 1 H) 6.86 (d, J=8.34 Hz, 1 H) 7.25 (s, 1 H).

Example 4

8-Isopropenyl-9,10-dimethoxy-5,8-dihydro-6H-[1,3]dioxolo[4,5-g]isoquino[3,2-a]isoquinoline

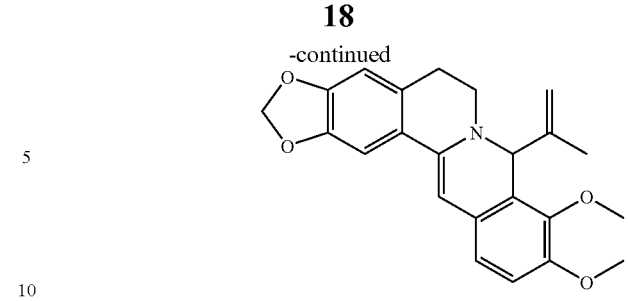

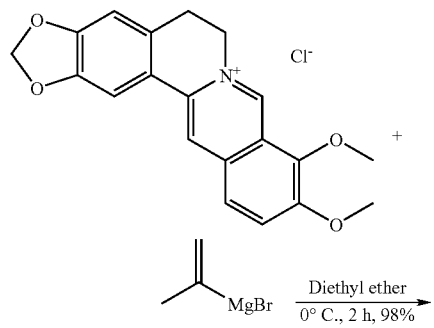

To a suspension of berberine hydrochloride (500 mg, 1.3 mmol) in anhydrous diethyl ether (100 mL) at 0° C. was added isopropenylmagnesium bromide solution (0.5 M in tetrahydrofuran, 52 mL, 26 mmol) dropwise. After stirring at 0° C. for 2 h, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 8-isopropenyl-9,10-dimethoxy-5,8-dihydro-6H-[1,3]dioxolo[4,5-g]isoquino[3,2-a]isoquinoline (500 mg, 98%). LC/MS m/e calcd for $C_{23}H_{23}NO_4$ $(M+H)^+$: 378.44, observed: 378.0; 1H NMR (400 MHz, DMSO-d6) δ ppm 1.57 (s, 3 H) 2.72-2.83 (m, 2 H) 3.00-3.09 (m, 1 H) 3.12-3.20 (m, 1 H) 3.71 (s, 3 H) 3.77 (s, 3 H) 4.61 (s, 1 H) 4.92 (d, J=1.52 Hz, 1 H) 5.19 (s, 1 H) 5.80 (s, 1 H) 6.00 (d, J=2.27 Hz, 2 H) 6.69 (d, J=8.59 Hz, 1 H) 6.77 (s, 1 H) 6.85 (d, J=8.34 Hz, 1 H) 7.23 (s, 1 H).

Example 5

8-Ethynyl-9,10-dimethoxy-5,8-dihydro-6H-[1,3]dioxolo[4,5-g]isoquino[3,2-a]isoquinoline

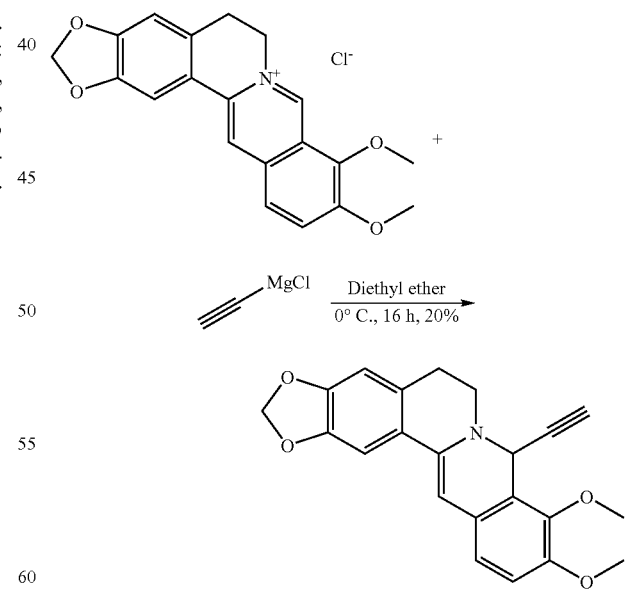

To a suspension of berberine hydrochloride (500 mg, 1.3 mmol) in anhydrous diethyl ether (50 mL) at 0° C. was added ethynylmagnesium chloride solution (1.1 M in tetrahydrofuran, 24 mL, 26 mmol) dropwise. After stirring at 0° C. for 16 h, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 8-ethynyl-9,10-dimethoxy-5,8-dihydro-6H-[1,3]dioxolo[4,5-g]isoquino[3,2-a]isoquinoline (95 mg, 20%). LC/MS m/e calcd for $C_{22}H_{19}NO_4$ $(M+H)^+$: 362.40, observed: 362.2; 1H NMR (400 MHz, DMSO-d6) δ ppm 2.78-2.88 (m, 2 H) 3.17 (d, J=2.27 Hz, 1 H) 3.21-3.30 (m, 2 H) 3.81 (d, J=4.80 Hz, 6 H) 5.45 (d, J=2.02 Hz, 1 H) 6.02 (d, J=5.81 Hz, 2 H) 6.18 (s, 1 H) 6.76-6.83 (m, 2 H) 6.93 (d, J=8.59 Hz, 1 H) 7.32 (s, 1 H).

Example 6

8-Allyl-9,10-dimethoxy-5,8-dihydro-6H-[1,3]dioxolo[4,5-g]isoquino[3,2-a]isoquinoline

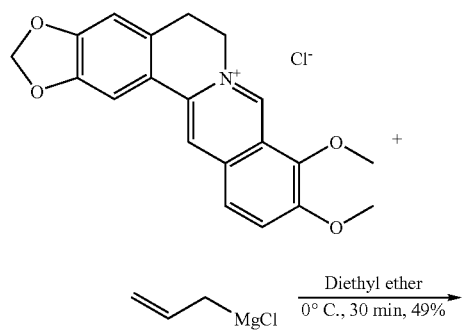

To a suspension of berberine hydrochloride (500 mg, 1.3 mmol) in anhydrous diethyl ether (50 mL) at 0° C. was added allylmagnesium chloride solution (1.7 M in tetrahydrofuran, 8 mL, 13 mmol) dropwise. After stirring at 0° C. for 30 min, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 8-allyl-9,10-dimethoxy-5,8-dihydro-6H-[1,3]dioxolo[4,5-g]isoquino[3,2-a]isoquinoline (250 mg, 49%). LC/MS m/e calcd for $C_{23}H_{23}NO_4$ $(M+H)^+$: 378.44, observed: 378.2; 1H NMR (400 MHz, DMSO-d6) δ ppm 2.34 (t, J=6.32 Hz, 2 H) 2.66-2.75 (m, 1 H) 2.79-2.87 (m, 1 H) 3.26-3.32 (m, 1 H) 3.35-3.44 (m, 1 H) 3.78 (d, J=6.32 Hz, 6 H) 4.78-4.85 (m, 2 H) 4.86 (s, 1 H) 5.68-5.80 (m, 1 H) 5.87 (s, 1 H) 6.00 (d, J=3.54 Hz, 2 H) 6.68 (d, J=8.34 Hz, 1 H) 6.77 (s, 1 H) 6.84 (d, J=8.59 Hz, 1 H) 7.23 (s, 1 H).

Example 7

9,10-Dimethoxy-8-prop-1-ynyl-5,8-dihydro-6H-[1,3]dioxolo[4,5-g]isoquino[3,2-a]isoquinoline

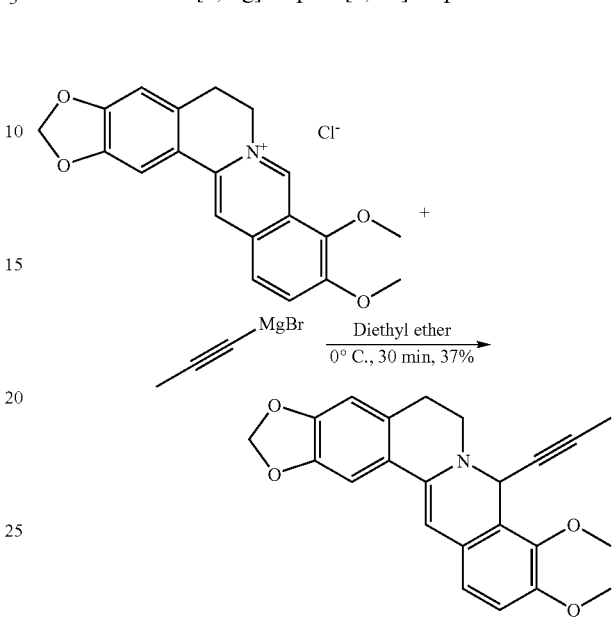

To a suspension of berberine hydrochloride (500 mg, 1.3 mmol) in anhydrous diethyl ether (100 mL) at 0° C. was added 1-propynylmagnesium bromide solution (0.5 M in tetrahydrofuran, 26 mL, 13 mmol) dropwise. After stirring at 0° C. for 30 min, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 9,10-dimethoxy-8-prop-1-ynyl-5,8-dihydro-6H-[1,3]dioxolo[4,5-g]isoquino[3,2-a]isoquinoline (190 mg, 37%). LC/MS m/e calcd for $C_{23}H_{21}NO_4$ $(M+H)^+$: 376.43, observed: 376.2; 1H NMR (400 MHz, DMSO-d6) δ ppm 1.68 (d, J=2.02 Hz, 3 H) 2.76-2.86 (m, 2 H) 3.21-3.30 (m, 2 H) 3.80 (d, J=3.03 Hz, 6 H) 5.39-5.43 (m, 1 H) 6.01 (d, J=5.31 Hz, 2 H) 6.15 (s, 1 H) 6.76 (d, 2 H) 6.90 (d, J=8.34 Hz, 1 H) 7.32 (s, 1 H).

Example 8

8-Isopropenyl-9,10-dimethoxy-13-methyl-5,8-dihydro-6H-[1,3]dioxolo[4,5-g]isoquino[3,2-a]isoquinoline

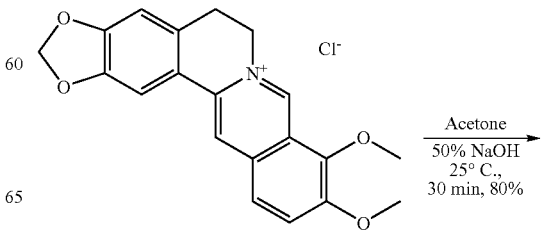

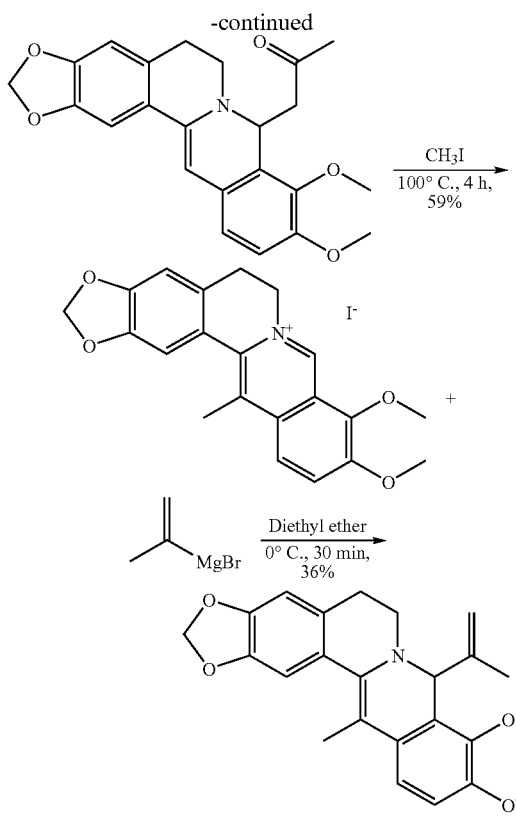

Berberine hydrochloride (10.0 g, 26.90 mmol), water (40 mL), acetone (10 mL), 50% aqueous sodium hydroxide (15 mL) was introduced into a reaction vessel. The reaction mixture was stirred vigorously for 30 min at room temperature. The resulting precipitate was collected and washed with 80% methanol (2×10 mL) and then dried to afford 1-(9,10-dimethoxy-5,8-dihydro-6H-[1,3]dioxolo[4,5-g]isoquino[3,2-a]isoquinolin-8-yl)-propan-2-one (8.5 g, 80%) as a yellow solid. LC/MS m/e calcd for $C_{23}H_{23}NO_5$ (M+H)$^+$: 394.44, observed: 336.0; 1H NMR (400 MHz, DMSO-d6) δ ppm 2.04 (s, 3 H) 2.31 (dd, J=14.65, 4.80 Hz, 1 H) 2.66-2.75 (m, 1 H) 2.75-2.82 (m, 1 H) 2.94 (dd, J=14.65, 6.57 Hz, 1 H) 3.16-3.25 (m, 1 H) 3.25-3.30 (m, 1 H) 3.77 (d, J=2.02 Hz, 6 H) 5.21 (dd, J=6.32, 4.80 Hz, 1 H) 5.97-6.03 (m, 3 H) 6.72 (d, J=8.34 Hz, 1 H) 6.76 (s, 1 H) 6.87 (d, J=8.34 Hz, 1 H) 7.25 (s, 1 H).

A mixture of 1-(9,10-dimethoxy-5,8-dihydro-6H-[1,3]dioxolo[4,5-g]isoquino[3,2-a]isoquinolin-8-yl)-propan-2-one (2.0 g, 5.1 mmol) and iodomethane (16 mL) was placed in a sealed tube and heated for 4 h at 100° C. After cooling to room temperature, methanol (100 mL) was added and the mixture was refluxed for 1 h. The mixture was cooled to 0° C. and the formed precipitate was collected by filtration. Re-crystallization from ethanol afforded 13-methyl-9,10-dimethoxy-5,6-dihydro-[1,3]dioxolo[4,5-g]isoquino[3,2-a]isoquinolin-7-ylium; iodide (1.44 g, 59%) as a yellow solid. LC/MS m/e calcd for $C_{21}H_{20}NO_4I$ (M+H)$^+$: 478.30, observed: 350.0; 1H NMR (400 MHz, DMSO-d6) δ ppm 2.94 (s, 3 H) 3.11 (m, 2 H) 4.10 (d, J=3.79 Hz, 6 H) 4.84 (m, 2 H) 6.19 (s, 2 H) 7.16 (s, 1 H) 7.48 (s, 1 H) 8.16-8.24 (m, 2 H) 9.89 (s, 1 H).

To a suspension of 9,10-dimethoxy-13-methyl-5,6-dihydro-[1,3]dioxolo[4,5-g]isoquino[3,2-a]isoquinolin-7-ylium; iodide (300 mg, 0.63 mmol) in anhydrous diethyl ether (100 mL) at 0° C. was added a solution of isopropenylmagnesium bromide in tetrahydrofuran (0.5 M, 18.8 mL, 9.4 mmol) dropwise. After stirring at 0° C. for 30 min, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 8-isopropenyl-9,10-dimethoxy-13-methyl-5,8-dihydro-6H-[1,3]dioxolo[4,5-g]isoquino[3,2-a]isoquinoline (90 mg, 36%). LC/MS m/e calcd for $C_{24}H_{23}NO_4$ (M+H)$^+$: 392.47, observed: 392.2; 1H NMR (400 MHz, DMSO-d6) δ ppm 1.53 (s, 3 H) 2.13 (s, 3 H) 2.62-2.71 (m, 1 H) 2.72-2.79 (m, 1 H) 3.00-3.08 (m, 1 H) 3.13-3.21 (m, 1 H) 3.71 (s, 3 H) 3.80 (s, 3 H) 4.59 (s, 1 H) 4.77 (s, 1 H) 5.12 (s, 1 H) 6.03 (s, 2 H) 6.83 (s, 1 H) 6.93 (s, 2 H) 7.02 (s, 1 H).

Example 9

9,10-Dimethoxy-13-methyl-8-prop-1-ynyl-5,8-dihydro-6H-[1,3]dioxolo[4,5-g]isoquino[3,2-a]isoquinoline

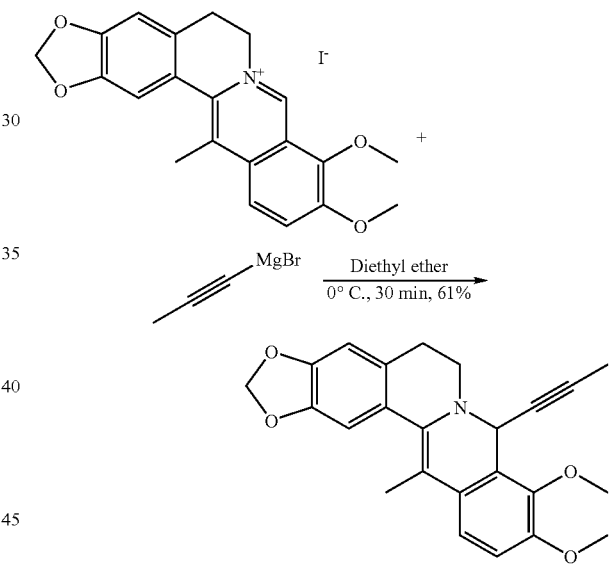

To a suspension of 9,10-dimethoxy-13-methyl-5,6-dihydro-[1,3]dioxolo[4,5-g]isoquino[3,2-a]isoquinolin-7-ylium; iodide (200 mg, 0.4 mmol) in anhydrous diethyl ether (5 mL) at 0° C. was added a solution of 1-propynylmagnesium bromide in tetrahydrofuran (0.5 M, 17 mL, 8.5 mmol) dropwise. After stirring at 0° C. for 30 min, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 9,10-dimethoxy-13-methyl-8-prop-1-ynyl-5,8-dihydro-6H-[1,3]dioxolo[4,5-g]isoquino[3,2-a]isoquinoline (100 mg, 61%). LC/MS m/e calcd for $C_{24}H_{23}NO_4$ (M+H)$^+$: 390.46, observed: 390.2; 1H NMR (400 MHz, DMSO-d6) δ ppm 1.67 (d, J=1.52 Hz, 3 H) 2.22 (s, 3 H) 2.59-2.69 (m, 1 H) 2.89-2.99 (m, 1 H) 3.16-3.27 (m, 2 H) 3.81 (d, J=7.58 Hz, 6 H) 5.38 (d, J=1.77 Hz, 1 H) 6.04 (d, J=2.78 Hz, 2 H) 6.84 (s, 1 H) 6.96 (m, 2 H) 7.06 (s, 1 H).

Example 10

13-Ethyl-8-isopropenyl-9,10-dimethoxy-5,8-dihydro-6H-[1,3]dioxolo[4,5-g]isoquino[3,2-a]isoquinoline

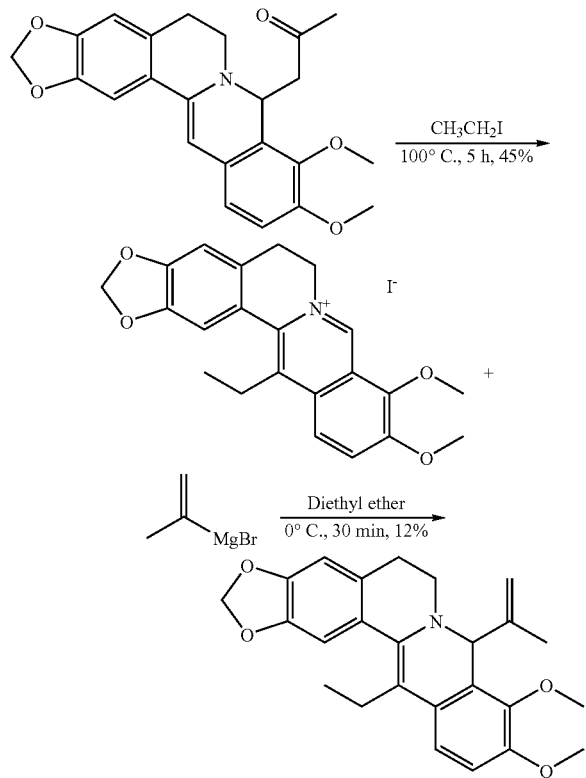

A mixture of 1-(9,10-dimethoxy-5,8-dihydro-6H-[1,3]dioxolo[4,5-g]isoquino[3,2-a]isoquinolin-8-yl)-propan-2-one (5.00 g, 12.71 mmol) and iodoethane (25 mL) was placed in a sealed tube and heated for 5 h at 100° C. After cooling to room temperature, methanol (400 mL) was added and the mixture was refluxed for 1 h. The mixture was cooled to 0° C. and the resulting suspension was collected by filtration. Re-crystallization from ethanol afforded 13-ethyl-9,10-dimethoxy-5,6-dihydro-[1,3]dioxolo[4,5-g]isoquino[3,2-a]isoquinolin-7-ylium; iodide (2.85 g, 45.7%) as a yellow solid. LC/MS m/e calcd for $C_{22}H_{22}NO_4I$ (M+H)$^+$: 492.32, observed: 364.1; 1H NMR (400 MHz, DMSO-d6) δ ppm 1.47 (t, J=7.33 Hz, 3 H) 3.10 (t, J=5.56 Hz, 2 H) 3.34-3.41 (m, 2 H) 4.11 (d, J=1.77 Hz, 6 H) 4.76-4.87 (m, 2 H) 6.20 (s, 2 H) 7.17 (s, 1 H) 7.31 (s, 1 H) 8.18-8.27 (m, 2 H) 9.90 (s, 1 H)

To a suspension of 13-ethyl-9,10-dimethoxy-5,6-dihydro-[1,3]dioxolo[4,5-g]isoquino[3,2-a]isoquinolin-7-ylium; iodide (300 mg, 0.61 mmol) in anhydrous diethyl ether (100 mL) at 0° C. was added a solution of isopropenylmagnesium bromide in tetrahydrofuran (0.5 M, 18.4 mL, 9.2 mmol) dropwise. After stirring at 0° C. for 30 min, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 13-ethyl-8-isopropenyl-9,10-dimethoxy-5,8-dihydro-6H-[1,3]dioxolo[4,5-g]isoquino[3,2-a]isoquinoline (32 mg, 12%). LC/MS m/e calcd for $C_{25}H_{27}NO_4$ (M+H)$^+$: 406.50, observed: 406.2; 1H NMR (400 MHz, DMSO-d6) δ ppm 1.16 (t, J=7.20 Hz, 3 H) 1.53 (s, 3 H) 2.57-2.64 (m, 1 H) 2.64-2.71 (m, 1 H) 2.64-2.71 (m, 1 H) 2.71-2.78 (m, 1 H) 2.95-3.04 (m, 1 H) 3.15-3.22 (m, 1 H) 3.72 (s, 3 H) 3.81 (s, 3 H) 4.60 (s, 1 H) 4.72 (s, 1 H) 5.08 (s, 1 H) 6.04 (d, J=4.55 Hz, 2 H) 6.86 (s, 1 H) 6.89 (s, 1 H) 6.96 (s, 2 H).

Example 11

8-Allyl-13-ethyl-9,10-dimethoxy-5,8-dihydro-6H-[1,3]dioxolo[4,5-g]isoquino[3,2-a]isoquinoline

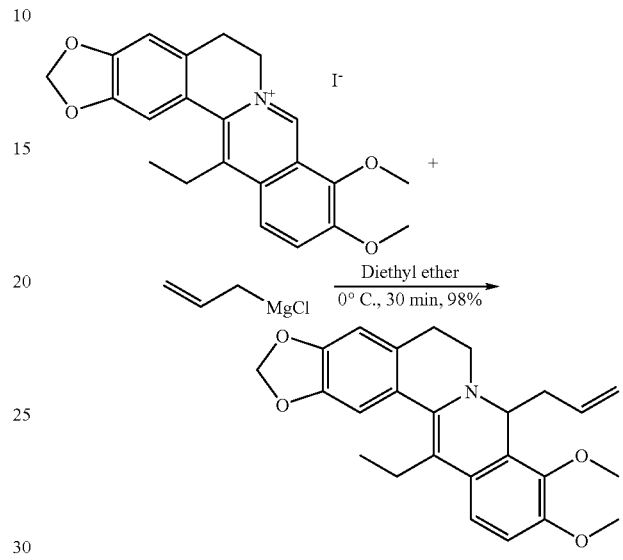

To a suspension of 13-ethyl-9,10-dimethoxy-5,6-dihydro-[1,3]dioxolo[4,5-g]isoquino[3,2-a]isoquinolin-7-ylium; iodide (200 mg, 0.4 mmol) in anhydrous diethyl ether (5 mL) at 0° C. was added a solution of allylmagnesium chloride in tetrahydrofuran (1.7 M, 2.5 mL, 4 mmol) dropwise. After stirring at 0° C. for 30 min, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 8-allyl-13-ethyl-9,10-dimethoxy-5,8-dihydro-6H-[1,3]dioxolo[4,5-g]isoquino[3,2-a]isoquinoline (160 mg, 98%). LC/MS m/e calcd for $C_{25}H_{27}NO_4$ (M+H)$^+$: 406.5, observed: 406.2; 1H NMR (400 MHz, DMSO-d6) δ ppm 1.18 (t, J=7.20 Hz, 3 H) 2.11-2.20 (m, 1 H) 2.25-2.35 (m, 1 H) 2.55-2.65 (m, 2 H) 2.66-2.76 (m, 2 H) 3.23-3.30 (m, 2 H) 3.80 (d, J=4.55 Hz, 6 H) 4.68-4.81 (m, 3 H) 5.63-5.75 (m, 1 H) 6.04 (d, J=11.87 Hz, 2 H) 6.85 (s, 1 H) 6.90 (s, 1 H) 6.94 (s, 2 H).

Example 12

13-Ethyl-9,10-dimethoxy-8-prop-1-ynyl-5,8-dihydro-6H-[1,3]dioxolo[4,5-g]isoquino[3,2-a]isoquinoline

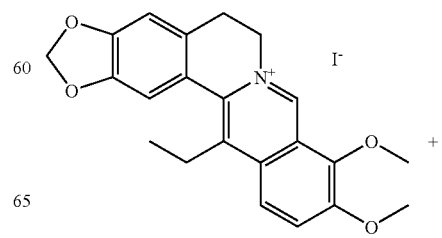

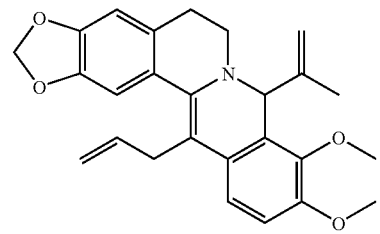

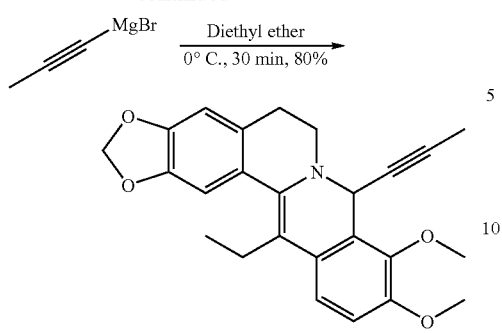

To a suspension of 13-ethyl-9,10-dimethoxy-5,6-dihydro-[1,3]dioxolo[4,5-g]isoquino[3,2-a]isoquinolin-7-ylium; iodide (200 mg, 0.4 mmol) in anhydrous diethyl ether (5 mL) at 0° C. was added a solution of 1-propynylmagnesium bromide solution in tetrahydrofuran (0.5 M, 8 mL, 4 mmol) dropwise. After stirring at 0° C. for 30 min, the reaction was quenched by adding saturated aqueous ammonium chloride solution (20 mL). The mixture was extracted with diethyl ether (2×50 mL), washed with brine, dried over anhydrous sodium sulfate and concentrated in vacuo. The residue was re-crystallized from diethyl ether to afford 13-ethyl-9,10-dimethoxy-8-prop-1-ynyl-5,8-dihydro-6H-[1,3]dioxolo[4,5-g]isoquino[3,2-a]isoquinoline (130 mg, 80%). LC/MS m/e calcd for $C_{25}H_{25}NO_4$ (M+H)+: 404.48, observed: 404.2; 1H NMR (400 MHz, DMSO-d6) δ ppm 1.20 (t, J=7.33 Hz, 3 H) 1.65 (d, J=2.02 Hz, 3 H) 2.60-2.81 (m, 4 H) 3.07 (m, 1 H) 3.18-3.25 (m, 1 H) 3.81 (d, J=8.84 Hz, 6 H) 5.32 (d, J=2.02 Hz, 1 H) 6.05 (d, J=6.32 Hz, 1 H) 6.86 (s, 1 H) 6.95 (s, 1 H) 6.96-7.02 (m, 2 H).

Example 13

13-Allyl-8-isopropenyl-9,10-dimethoxy-5,8-dihydro-6H-[1,3]dioxolo[4,5-g]isoquino[3,2-a]isoquinoline

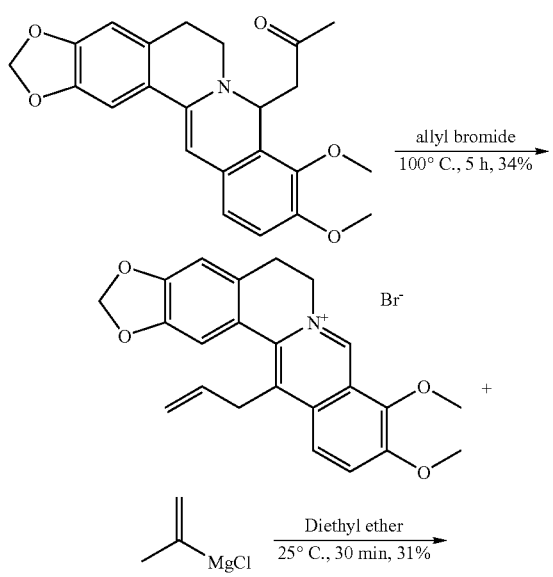

A mixture of 1-(9,10-dimethoxy-5,8-dihydro-6H-[1,3]dioxolo[4,5-g]isoquino[3,2-a]isoquinolin-8-yl)-propan-2-one (2.0 g, 5.08 mmol) and allyl bromide (10 mL) was placed in a sealed tube and heated for 5 h at 100° C. After cooling, ethanol (200 mL) was added and the mixture was refluxed for 10 min. After cooling, the resulting precipitate was collected by filtration. Re-crystallization from ethanol afforded 13-allyl-9,10-dimethoxy-5,6-dihydro-[1,3]dioxolo[4,5-g]isoquino[3,2-a]isoquinolin-7-ylium; bromide (0.80 g, 34%) LC/MS m/e calcd for $C_{23}H_{22}NO_4Br$ (M+H)+: 457.34, observed: 376.1; 1H NMR (400 MHz, DMSO-d6) δ ppm 3.12 (t, J=5.56 Hz, 2 H) 4.01-4.07 (m, 2 H) 4.10 (d, J=12.13 Hz, 6 H) 4.81-4.91 (m, 3 H) 5.38 (d, J=10.36 Hz, 1 H) 6.18 (s, 2 H) 6.40-6.51 (m, 1 H) 7.18 (s, 1 H) 7.36 (s, 1 H) 8.01 (d, J=9.35 Hz, 1 H) 8.20 (d, J=9.35 Hz, 1 H) 10.00 (s, 1 H).

To a suspension of 13-allyl-9,10-dimethoxy-5,6-dihydro-[1,3]dioxolo[4,5-g]isoquino[3,2-a]isoquinolin-7-ylium; bromide (300 mg, 0.66 mmol) in anhydrous diethyl ether (20 mL) at 0° C. was added a solution of isopropenylmagnesium bromide in tetrahydrofuran (0.5 M, 20 mL, 10 mmol) dropwise. After stirring at 0° C. for 30 min, the reaction was quenched by adding saturated aqueous ammonium chloride solution (50 mL). The mixture was extracted with diethyl ether (2×100 mL), washed with brine, dried over anhydrous sodium sulfate and concentrated in vacuo. The residue was re-crystallized from diethyl ether to afford 13-allyl-8-isopropenyl-9,10-dimethoxy-5,8-dihydro-6H-[1,3]dioxolo[4,5-g]isoquino[3,2-a]isoquinoline (75 mg, 27%). LC/MS m/e calcd for $C_{26}H_{27}NO_4$ (M+H)+: 418.51, observed: 418.2; 1H NMR (400 MHz, DMSO-d6) δ ppm 1.57 (s, 3 H) 2.64-2.80 (m, 2 H) 2.97-3.06 (m, 1 H) 3.18-3.25 (m, 1 H) 3.72 (s, 3 H) 3.79 (s, 3 H) 4.63 (s, 1 H) 4.73 (s, 1 H) 5.06-5.18 (m, 3 H) 6.02 (s, 2 H) 6.05-6.15 (m, 1 H) 6.81 (m, 1 H) 6.86 (s, 1 H) 6.91 (m, 1 H) 6.98 (s, 1 H).

Example 14

9,10-Dimethoxy-8,8,13-trimethyl-5,8-dihydro-6H-[1,3]dioxolo[4,5-g]isoquino[3,2-a]isoquinoline

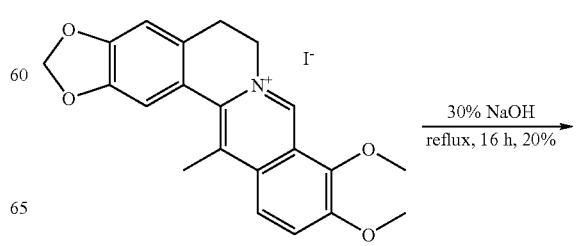

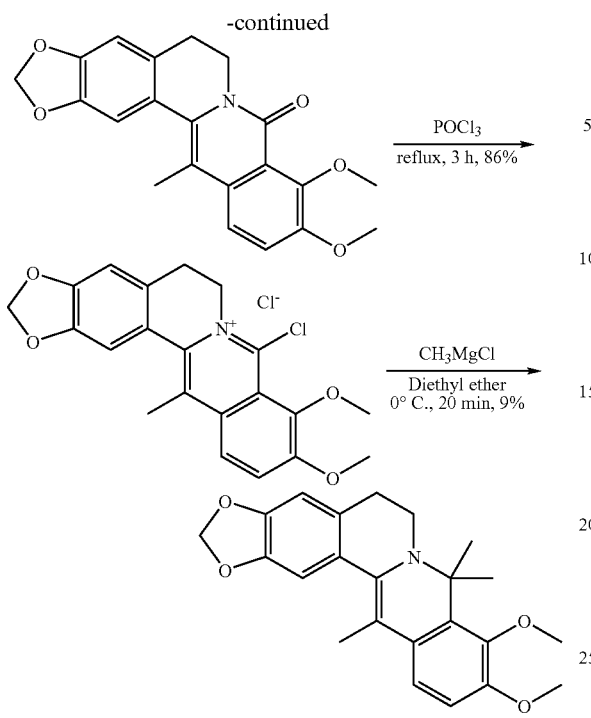

A mixture of 9,10-dimethoxy-13-methyl-5,6-dihydro[1,3]dioxolo[4,5-g]isoquino[3,2-a]isoquinolin-7-ylium; iodide (0.95 g, 2.0 mmol) and 30% sodium hydroxide in water (150 mL) was refluxed for 16 h. The precipitate was collected and treated with hot 3% hydrochloric acid. Purification by flash silica gel chromatography (silica gel from QingDao, 100-200 mesh, glass column from Shanghai SD company) (50% dichloromethane/ethyl acetate) afforded 9,10-dimethoxy-13-methyl-5,6-dihydro-[1,3]dioxolo[4,5-g]isoquino[3,2-a]isoquinolin-8-one (150 mg. 20%) LC/MS m/e calcd for $C_{21}H_{19}NO_5$ (M+H)$^+$: 366.69, observed: 366.1; 1H NMR (400 MHz, DMSO-d6) δ ppm 2.46 (s, 3 H) 2.80 (t, J=5.56 Hz, 2 H) 3.78 (s, 3 H) 3.90 (s, 3 H) 3.96-4.07 (m, 2 H) 6.09 (s, 2 H) 7.00 (s, 1 H) 7.16 (s, 1 H) 7.54-7.61 (m, 2 H).

A mixture of 9,10-dimethoxy-13-methyl-5,6-dihydro-[1,3]dioxolo[4,5-g]isoquino[3,2-a]isoquinolin-8-one (970 mg, 2.66 mmol) and phosphorus oxychloride (20 ml) was refluxed for 3 h. After cooling, the mixture was concentrated in vacuo to afford 8-chloro-9,10-dimethoxy-13-methyl-5,6-dihydro-[1,3]dioxolo[4,5-g]isoquino[3,2-a]isoquinolin-7-ylium; chloride (970 mg, 86%) as a solid which was used for next step without further purification. LC/MS m/e calcd for $C_{21}H_{19}Cl_2NO_4$ (M+H)$^+$: 421.29, To a suspension of 8-chloro-9,10-dimethoxy-13-methyl-5,6-dihydro-[1,3]dioxolo[4,5-g]isoquino[3,2-a]isoquinolin-7-ylium; chloride (970 mg, 2.3 mmol) in anhydrous diethyl ether (150 mL) at 0° C. was added a solution of methylmagnesium chloride in tetrahydrofuran (3 M, 15 mL, 45 mmol) dropwise. After stirring at 0° C. for 30 min, the reaction was quenched by adding saturated aqueous ammonium chloride solution (50 mL). The mixture was extracted with diethyl ether (2×100 mL), washed with brine, dried over anhydrous sodium sulfate and concentrated in vacuo. The residue was re-crystallized from diethyl ether to afford 9,10-dimethoxy-8,8,13-trimethyl-5,8-dihydro-6H-[1,3]dioxolo[4,5-g]isoquino[3,2-a]isoquinoline (80 mg, 9%). LC/MS m/e calcd for $C_{23}H_{25}NO_4$ (M+H)$^+$: 380.46, observed: 380.1; 1H NMR (400 MHz, DMSO-d6) δ ppm 1.56 (s, 6 H) 2.12 (s, 3 H) 2.63 (t, J=5.18 Hz, 2 H) 3.16 (t, J=5.31 Hz, 2 H) 3.73 (s, 3 H) 3.79 (s, 3 H) 6.01 (s, 2 H) 6.81 (s, 1 H) 6.86-6.93 (m, 2 H) 6.98 (s, 1 H).

Example 15

8,8-Diethyl-9,10-dimethoxy-13-methyl-5,8-dihydro-6H-[1,3]dioxolo[4,5-g]isoquino[3,2-a]isoquinoline

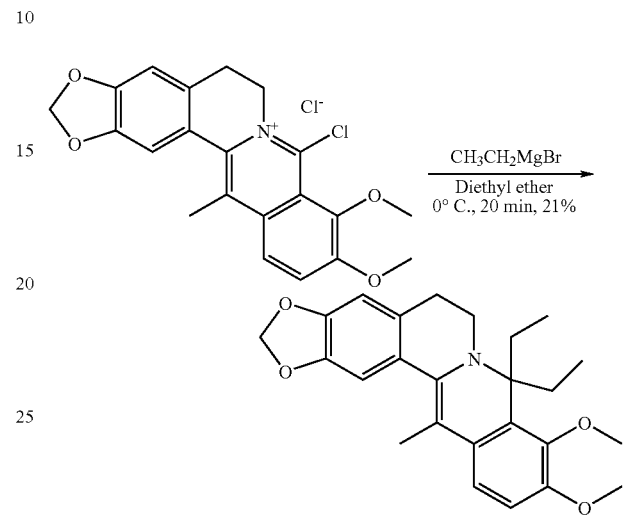

To a suspension of 8-chloro-9,10-dimethoxy-13-methyl-5,6-dihydro-[1,3]dioxolo[4,5-g]isoquino[3,2-a]isoquinolin-7-ylium; chloride (1050 mg, 2.5 mmol) in anhydrous diethyl ether (50 mL) at 0° C. was added a solution of ethylmagnesium bromide in tetrahydrofuran (3 M, 9 mL, 27.4 mmol) dropwise. After stirring at 0° C. for 20 min, the reaction was quenched by adding saturated aqueous ammonium chloride solution (50 mL). The mixture was extracted with diethyl ether (2×100 mL), washed with brine, dried over anhydrous sodium sulfate and concentrated in vacuo. The residue was re-crystallized from diethyl ether to afford 8,8-diethyl-9,10-dimethoxy-13-methyl-5,8-dihydro-6H-[1,3]dioxolo[4,5-g]isoquino[3,2-a]isoquinoline (220 mg, 21%).

LC/MS m/e calcd for $C_{25}H_{29}NO_4$ (M+H)$^+$: 408.51, observed: 408.2; 1H NMR (400 MHz, DMSO-d6) δ ppm 0.76 (t, J=7.33 Hz, 6 H) 1.79-1.91 (m, 2 H) 1.97 (s, 3 H) 2.09-2.21 (m, 2 H) 2.70 (m, 2 H) 3.06 (m, 2 H) 3.70-3.81 (m, 6 H) 6.02 (s, 2 H) 6.70 (d, J=8.59 Hz, 1 H) 6.80 (s, 1 H) 6.88 (d, J=8.84 Hz, 1 H) 6.90 (s, 1 H).

Example 16

13-Ethyl-9,10-dimethoxy-8,8-dimethyl-5,8-dihydro-6H-[1,3]dioxolo[4,5-g]isoquino[3,2-a]isoquinoline

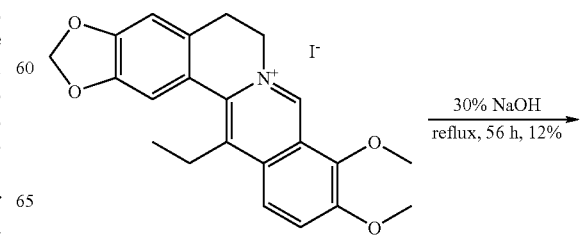

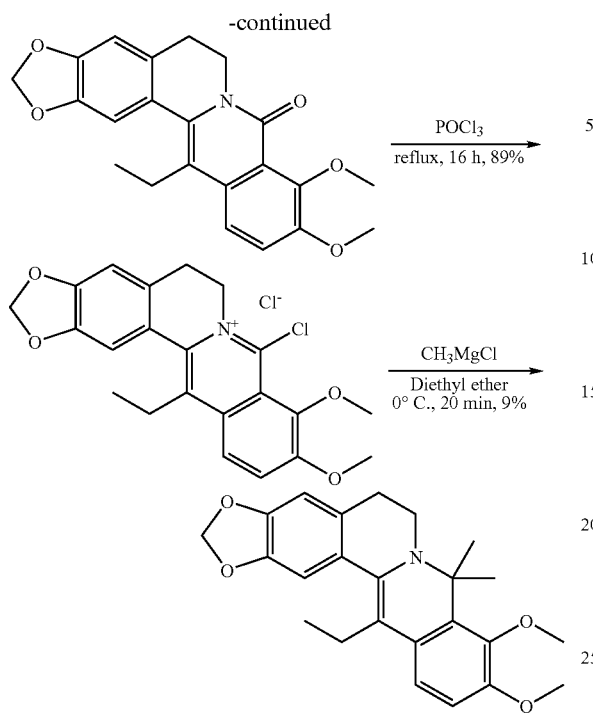

A mixture of 13-ethyl-9,10-dimethoxy-5,6-dihydro[1,3]dioxolo[4,5-g]isoquino[3,2-a]isoquinolin-7-ylium; iodide (1.1 g, 2.2 mmol) and 30% sodium hydroxide in water (150 mL) was refluxed for 56 h. The precipitate formed was collected and treated with hot 3% hydrochloric acid. The precipitate was collected and re-crystallized from ethanol to afford 13-ethyl-9,10-dimethoxy-5,6-dihydro-[1,3]dioxolo[4,5-g]isoquino[3,2-a]isoquinolin-8-one (100 mg. 12%).

LC/MS m/e calcd for $C_{22}H_{21}NO_5$ (M+H)$^+$: 380.42, observed: 380.2; 1H NMR (400 MHz, chloroform-d) δ ppm 1.44 (t, J=7.33 Hz, 3 H) 2.80 (t, J=5.68 Hz, 2 H) 3.03 (q, J=7.49 Hz, 2 H) 3.99 (s, 3 H) 4.03 (s, 3 H) 4.17-4.32 (m, 2 H) 6.05 (s, 2 H) 6.79 (s, 1 H) 7.11 (s, 1 H) 7.41 (d, J=9.09 Hz, 1 H) 7.59 (d, J=9.09 Hz, 1 H).

A mixture of 13-ethyl-9,10-dimethoxy-5,6-dihydro-[1,3]dioxolo[4,5-g]isoquino[3,2-a]isoquinolin-8-one (60 mg, 0.16 mmol) and phosphorus oxychloride (3 ml) was refluxed for 16 h. After cooling, the mixture was concentrated in vacuo to afford 8-chloro-13-ethyl-9,10-dimethoxy-5,6-dihydro-[1,3]dioxolo[4,5-g]isoquino[3,2-a]isoquinolin-7-ylium; chloride (62 mg, 89%) as a solid which was used for next step without further purification. LC/MS m/e calcd for $C_{22}H_{21}Cl_2NO_4$ (M+H)$^+$: 435.32; 1H NMR (400 MHz, Chloroform-d) δ ppm 1.47-1.60 (m, 3 H) 3.07-3.29 (m, 2 H) 3.32-3.55 (m, 2 H) 4.15 (d, J=6.82 Hz, 6 H) 4.94 (s, 2 H) 6.13 (s, 2 H) 6.94 (s, 1 H) 7.06 (s, 1 H) 8.01 (d, J=9.35 Hz, 1 H) 8.15 (d, J=9.35 Hz, 1 H).

To a suspension of 8-chloro-13-ethyl-9,10-dimethoxy-5,6-dihydro-[1,3]dioxolo[4,5-g]isoquino[3,2-a]isoquinolin-7-ylium; chloride (62 mg, 0.14 mmol) in anhydrous diethyl ether (10 mL) at 0° C. was added a solution of methylmagnesium chloride in tetrahydrofuran (3 M, 18 mL, 54 mmol) dropwise. After stirring at 0° C. for 20 min, the reaction was quenched by adding saturated aqueous ammonium chloride solution (50 mL). The mixture was extracted with diethyl ether (2×100 mL), washed with brine, dried over anhydrous sodium sulfate and concentrated in vacuo. The residue was re-crystallized from diethyl ether to afford 13-ethyl-9,10-dimethoxy-8,8-dimethyl-5,8-dihydro-6H-[1,3]dioxolo[4,5-g]isoquino[3,2-a]isoquinoline (5 mg, 9%). LC/MS m/e calcd for $C_{24}H_{27}NO_4$ (M+H)$^+$: 394.49, observed: 394.1; 1H NMR (400 MHz, DMSO-d6) δ ppm 1.14 (t, J=7.20 Hz, 3 H) 1.50 (s, 6 H) 2.60 (t, J=5.31 Hz, 2 H) 2.65-2.72 (m, 2 H) 3.12 (t, J=5.68 Hz, 2 H) 3.71 (s, 3 H) 3.80 (s, 3 H) 6.02 (s, 2 H) 6.84 (s, 1 H) 6.88 (s, 1 H) 6.94 (m, 1 H) 6.99 (m, 1 H).

Example 17

8,8-Diallyl-9,10-dimethoxy-5,8-dihydro-6H-[1,3]dioxolo[4,5-g]isoquino[3,2-a]isoquinoline

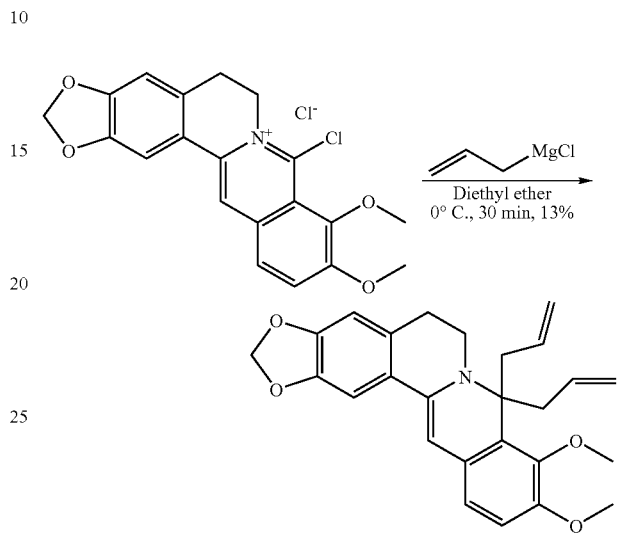

To a suspension of 8-chloro-9,10-dimethoxy-5,6-dihydro-[1,3]dioxolo[4,5-g]isoquino[3,2-a]isoquinolin-7-ylium; chloride (0.2 g, 0.5 mmol) in anhydrous diethyl ether (5 mL) at 0° C. was added a solution of allylmagnesium chloride in tetrahydrofuran (1.3 M, 2.16 mL, 4 mmol) dropwise. After stirring at 0° C. for 30 min, the reaction was quenched by adding saturated aqueous ammonium chloride solution (10 mL). The mixture was extracted with diethyl ether (2×50 mL), washed with brine, dried over anhydrous sodium sulfate and concentrated in vacuo. The residue was re-crystallized from diethyl ether to afford 8,8-diallyl-9,10-dimethoxy-5,8-dihydro-6H-[1,3]dioxolo[4,5-g]isoquino[3,2-a]isoquinoline (28 mg, 13%). LC/MS m/e calcd for $C_{26}H_{27}NO_4$ (M+H)$^+$: 418.51, observed: 418.3; 1H NMR (400 MHz, DMSO-d6) δ ppm 2.66-2.78 (m, 4 H) 2.94 (dd, J=15.41, 6.06 Hz, 2 H) 3.26 (t, J=5.43 Hz, 2 H) 3.77 (d, J=10.36 Hz, 6 H) 4.88 (d, J=10.36 Hz, 2 H) 4.98 (d, J=17.43 Hz, 2 H) 5.35 (s, 1 H) 5.66-5.78 (m, J=16.99, 10.29, 7.07, 6.82 Hz, 2 H) 5.98 (s, 2 H) 6.51 (d, J=8.34 Hz, 1 H) 6.72 (s, 1 H) 6.80 (d, J=8.34 Hz, 1 H) 7.15 (s, 1 H).

Example 18

13-Benzyl-9,10-dimethoxy-8,8-dimethyl-5,8-dihydro-6H-[1,3]dioxolo[4,5-g]isoquino[3,2-a]isoquinoline

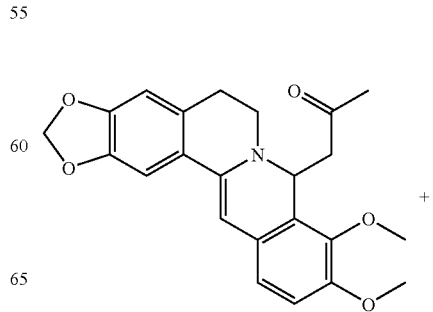

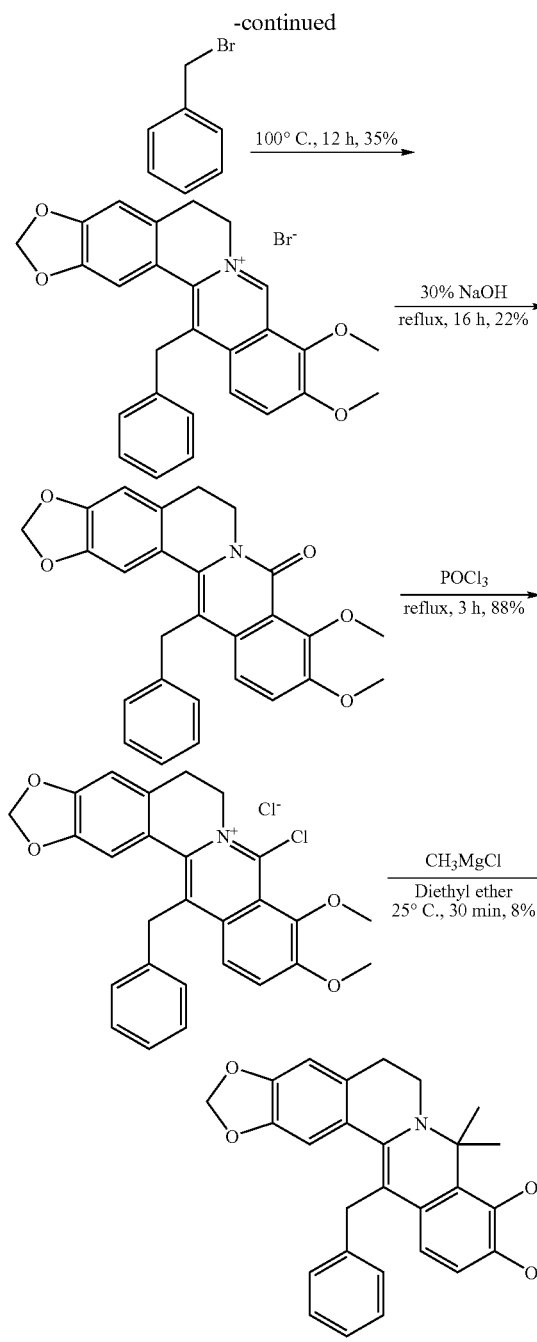

A mixture of 1-(9,10-dimethoxy-5,8-dihydro-6H-[1,3]dioxolo[4,5-g]isoquino[3,2-a]isoquinolin-8-yl)-propan-2-one (2.0 g, 5.1 mmol) and bromomethyl-benzene (10 mL) was placed in a sealed tube and heated for 12 h at 100° C. After cooling to room temperature, methanol (100 mL) was added and the mixture was refluxed for 1 h. The mixture was cooled to 0° C. and the resulting precipitate was collected and re-crystallized from ethanol to afford 13-benzyl-9,10-dimethoxy-5,6-dihydro[1,3]dioxolo[4,5-g]isoquino[3,2-a]isoquinolin-7-ylium; bromide (0.92 g, 35%) as a yellow solid. LC/MS m/e calcd for $C_{27}H_{24}NO_4Br$ (M+H)$^+$: 506.40, observed: 426.1; 1H NMR (400 MHz, DMSO-d6) δ ppm 3.12-3.22 (m, 2 H) 4.03 (s, 3 H) 4.12 (s, 3 H) 4.76 (s, 2 H) 4.83-4.96 (m, 2 H) 6.09 (s, 2 H) 6.97 (s, 1 H) 7.13-7.22 (m, 3 H) 7.29 (t, J=7.20 Hz, 1 H) 7.38 (t, J=7.45 Hz, 2 H) 7.79 (d, J=9.35 Hz, 1 H) 8.10 (d, J=9.60 Hz, 1 H) 10.05 (s, 1 H).

A mixture of 13-benzyl-9,10-dimethoxy-5,6-dihydro[1,3]dioxolo[4,5-g]isoquino[3,2-a]isoquinolin-7-ylium; bromide (0.9 g, 1.8 mmol) and 30% sodium hydroxide in water (150 mL) was refluxed for 16 h. The precipitate was collected and treated with hot 3% hydrochloric acid. The residue was re-crystallized from ethanol to afford 13-benzyl-9,10-dimethoxy-5,6-dihydro-[1,3]dioxolo[4,5-g]isoquino[3,2-a]isoquinolin-8-one (180 mg. 22%) LC/MS m/e calcd for $C_{27}H_{23}NO_5$ (M+H)$^+$: 442.49, observed: 442.1.

A mixture of 13-benzyl-9,10-dimethoxy-5,6-dihydro-[1,3]dioxolo[4,5-g]isoquino[3,2-a]isoquinolin-8-one (180 mg, 0.4 mmol) and phosphorus oxychloride (10 ml) was refluxed for 3 h. After cooling, the mixture was concentrated in vacuo to afford 13-benzyl-8-chloro-9,10-dimethoxy-5,6-dihydro-[1,3]dioxolo[4,5-g]isoquino[3,2-a]isoquinolin-7-ylium; chloride (176 mg, 88%) as a solid which was used for next step without further purification. LC/MS m/e calcd for $C_{22}H_{21}Cl_2NO_4$ (M+H)$^+$: 497.39.

To a suspension of 13-benzyl-8-chloro-9,10-dimethoxy-5,6-dihydro-[1,3]dioxolo[4,5-g]isoquino[3,2-a]isoquinolin-7-ylium; chloride (176 mg, 0.35 mmol) in anhydrous diethyl ether (10 mL) at 0° C. was added a solution of methylmagnesium chloride in tetrahydrofuran (3 M, 1.4 mL, 4 mmol) dropwise. After stirring at 0° C. for 30 min, the reaction was quenched by adding saturated aqueous ammonium chloride solution (50 mL). The mixture was extracted with diethyl ether (2×100 mL), washed with brine, dried over anhydrous sodium sulfate and concentrated in vacuo. The residue was re-crystallized from diethyl ether to afford 13-benzyl-9,10-dimethoxy-8,8-dimethyl-5,8-dihydro-6H-[1,3]dioxolo[4,5-g]isoquino[3,2-a]isoquinoline (13 mg, 8%). LC/MS m/e calcd for $C_{29}H_{29}NO_4$ (M+H)$^+$: 456.56, observed: 456.3; 1H NMR (400 MHz, DMSO-d6) δ ppm 1.65 (s, 6 H) 2.66-2.72 (m, 2 H) 3.20-3.27 (m, 2 H) 3.73 (d, J=2.53 Hz, 6 H) 4.05 (s, 2 H) 5.93 (s, 2 H) 6.71 (m, 2 H) 6.77 (m, 1 H) 6.86 (s, 1 H) 7.15-7.26 (m, 3 H) 7.31 (t, J=7.45 Hz, 2 H).

Example 19

12-Chloro-9,10-dimethoxy-8,8-dimethyl-5,8-dihydro-6H-[1,3]dioxolo[4,5-g]isoquino[3,2-a]isoquinoline

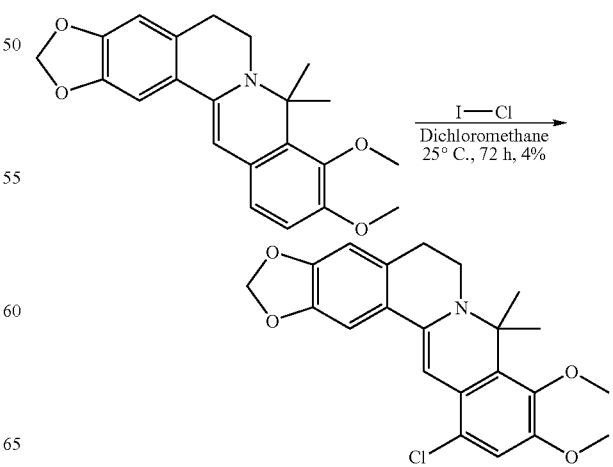

To a solution of 9,10-dimethoxy-8,8-dimethyl-5,8-dihydro-6H-[1,3]dioxolo[4,5-g]isoquino[3,2-a]isoquinoline (182 mg, 0.5 mmol) in anhydrous dichloromethane (20 mL) at 25° C. was added Iodine monochloride (0.57 g, 3.5 mmol). After stirring in the dark at 25° C. for 72 h, the reaction was washed twice with aqueous 10% sodium thiosulfate solution (2×50 mL) to remove excessive iodine monochloride, dried over anhydrous sodium sulfate and concentrated in vacuo. Purification by Waters Automated Flash System (column: Xterra 30 mm×100 mm, sample manager 2767, pump 2525, detector: ZQ mass and UV 2487, solvent system: acetonitrile and 0.1% ammonium hydroxide in water) afforded 12-chloro-9,10-dimethoxy-8,8-dimethyl-5,8-dihydro-6H-[1,3]dioxolo[4,5-g]isoquino[3,2-a]isoquinoline (9.6 mg, 4%). LC/MS m/e calcd for $C_{22}H_{22}ClNO_4$ (M+H)$^+$: 400.88, observed: 400.1; 1H NMR (400 MHz, MeOD) δ ppm 2.05 (s, 6 H) 3.14 (m, 2 H) 3.93 (s, 3 H) 4.01 (s, 3 H) 4.23 (m, 2 H) 6.22 (s, 2 H) 7.04 (s, 1 H) 7.32 (s., 1 H) 7.63 (s, 1 H).

Example 20

9',10'-Dimethoxy-5',6'-dihydrospiro[cyclopentane-1, 8'-[1,3]dioxolo[4,5-g]isoquino[3,2-a]isoquinoline]

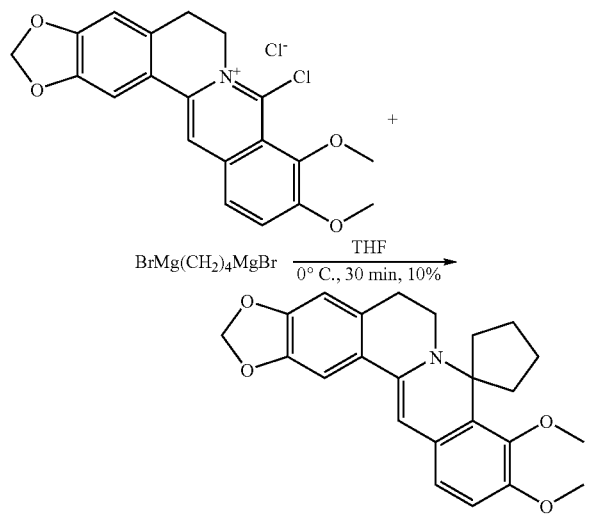

To a suspension of 8-chloro-9,10-dimethoxy-5,6-dihydro-[1,3]dioxolo[4,5-g]isoquino[3,2-a]isoquinolin-7-ylium; chloride (1.34 g, 3.3 mmol) in anhydrous tetrahydrofuran (100 mL) at 0° C. was added butyl-1,4-dimagnesium bromide solution (3 M in tetrahydrofuran, 17.4 mL, 4.95 mmol) dropwise. After stirring at 0° C. for 30 min, the reaction was quenched by adding saturated aqueous ammonium chloride solution (30 mL). The mixture was extracted with diethyl ether (2×100 mL), washed with brine, dried over anhydrous sodium sulfate and concentrated in vacuo. The residue was re-crystallized from methanol to afford 9',10'-dimethoxy-5', 6'-dihydrospiro[cyclopentane-1,8'-[1,3]dioxolo[4,5-g]isoquino[3,2-a]isoquinoline] (120 mg, 10%). LC/MS m/e calcd for $C_{24}H_{25}NO_4$ (M+H)$^+$: 392.47, observed: 392.2; 1H NMR (400 MHz, Chloroform-d) δ ppm 1.84-1.97 (m, 2 H) 1.97-2.09 (m, 2 H) 2.18-2.30 (m, 2 H) 2.37-2.49 (m, 2 H) 2.82 (t, J=5.56 Hz, 2 H) 3.31 (t, J=5.56 Hz, 2 H) 3.85 (s, 3 H) 3.88 (s, 3 H) 5.73 (s, 1 H) 5.95 (s, 2 H) 6.58 (s, 1 H) 6.64 (d, J=8.34 Hz, 1 H) 6.75 (d, J=8.34 Hz, 1 H) 7.16 (s, 1 H).

Example 21

9,10-Dimethoxy-8,8-dimethyl-5,8,13,13a-tetrahydro-6H-[1,3]dioxolo[4,5-g]isoquino[3,2-a]isoquinoline

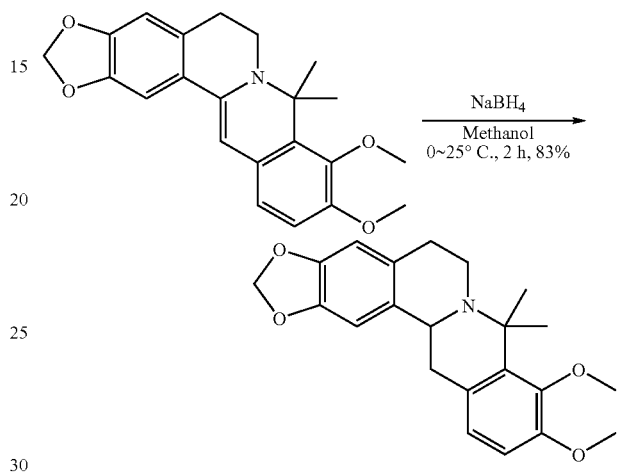

To a solution of 9,10-dimethoxy-8,8-dimethyl-5,8-dihydro-6H-[1,3]dioxolo[4,5-g]isoquino[3,2-a]isoquinoline (600 mg, 1.64 mmol) in methanol (50 mL) was added sodium borohydride (65 mg, 1.7 mmol) in small portions at 0° C. After stirring at 0° C. for 2 h, the mixture was concentrated in vacuo. The resulting residue was extracted with diethyl ether (2×50 mL), washed with water (2×25 mL), dried over anhydrous sodium sulfate and concentrated in vacuo to afford 9,10-dimethoxy-8,8-dimethyl-5,8,13,13a-tetrahydro-6H-[1, 3]dioxolo[4,5-g]isoquino[3,2-a]isoquinoline (0.5 g, 83%). LC/MS m/e calcd for $C_{22}H_{25}NO_4$ (M+H)$^+$: 368.45, observed: 368.1; 1H NMR (400 MHz, MeOD) δ ppm 1.51 (s, 3 H) 1.72 (s, 3 H) 2.63-2.84 (m, 3 H) 2.84-2.93 (m, 1 H) 3.06 (dd, J=16.17, 3.79 Hz, 1 H) 3.21-3.28 (m, 1 H) 3.83 (s, 3 H) 3.86 (s, 3 H) 4.09 (dd, J=11.37, 3.54 Hz, 1 H) 5.88 (s, 2 H) 6.58 (s, 1 H) 6.75 (s, 1 H) 6.80-6.85 (m, 1 H) 6.86-6.91 (m, 1 H).

Example 22

9,10-Dimethoxy-8,8,13-trimethyl-5,8,13,13a-tetrahydro-6H-[1,3]dioxolo[4,5-g]isoquino[3,2-a]isoquinoline

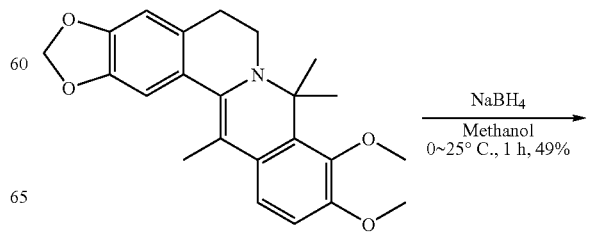

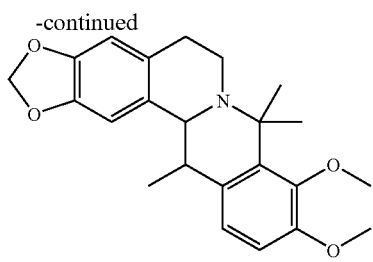

To a solution of 9,10-dimethoxy-8,8,13-trimethyl-5,8-dihydro-6H-[1,3]dioxolo[4,5-g]isoquino[3,2-a]isoquinoline (60 mg, 0.16 mmol) in methanol (10 mL) was added sodium borohydride (15 mg, 0.39 mmol) in small portions at 0° C. After stirring at 0° C. for 1 h, the reaction solvent was concentracted (? concentrated?) in vacuo. The resulting residue was extracted with diethyl ether (2×50 mL), washed with water (2×25 mL), dried over anhydrous sodium sulfate and concentrated in vacuo. The residue was re-crystallized from methanol to afford 9,10-dimethoxy-8,8,13-trimethyl-5,8,13,13a-tetrahydro-6H-[1,3]dioxolo[4,5-g]isoquino[3,2-a]isoquinoline (30 mg, 49%). LC/MS m/e calcd for $C_{23}H_{27}NO_4$ (M+H)$^+$: 382.48, observed: 382.2; 1H NMR (400 MHz, DMSO-d6) δ ppm 0.78 (d, J=6.82 Hz, 3 H) 1.41 (s, 3 H) 1.57 (s, 3 H) 2.31-2.40 (m, 1 H) 2.55-2.62 (m, 1 H) 2.66-2.75 (m, 1 H) 2.94-3.02 (m, 1 H) 3.23-3.30 (m, 1 H) 3.79 (d, J=6.06 Hz, 6 H) 4.03 (s, 1 H) 5.95 (d, J=3.28 Hz, 2 H) 6.66 (s, 1 H) 6.81 (m, 2 H) 6.93 (d, J=8.59 Hz, 1 H).

Example 23

8,8-Diethyl-9,10-dimethoxy-13-methyl-5,8,13,13a-tetrahydro-6H-[1,3]dioxolo[4,5-g]isoquino[3,2-a]isoquinoline

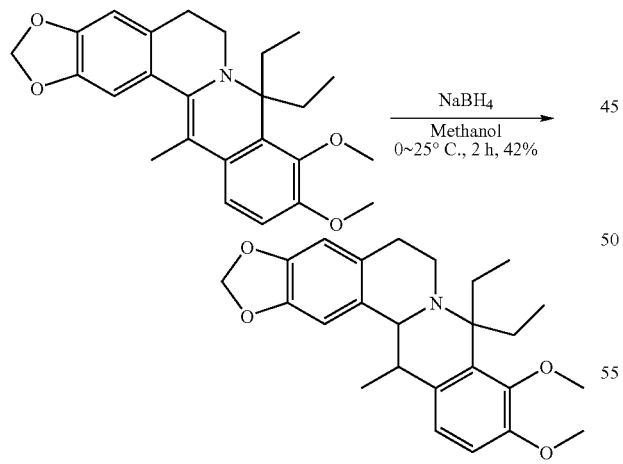

To a solution of 8,8-diethyl-9,10-dimethoxy-13-methyl-5,8-dihydro-6H-[1,3]dioxolo[4,5-g]isoquino[3,2-a]isoquinoline (100 mg, 0.25 mmol) in methanol (10 mL) was added sodium borohydride (23 mg, 0.61 mmol) in small portions at 0° C. After stirring at 0° C. for 2 h, the mixture was concentrated in vacuo. The resulting residue was extracted with diethyl ether (2×50 mL), washed with water (2×25 mL), dried over anhydrous sodium sulfate and concentrated in vacuo. The residue was re-crystallized from methanol to afford 8,8-diethyl-9,10-dimethoxy-13-methyl-5,8,13,13a-tetrahydro-6H-[1,3]dioxolo[4,5-g]isoquino[3,2-a]isoquinoline (43 mg, 42%). LC/MS m/e calcd for $C_{25}H_{31}NO_4$ (M+H)$^+$: 410.53, observed: 410.2; 1H NMR (400 MHz, DMSO-d6) δ ppm 0.48 (t, J=7.33 Hz, 3 H) 0.75 (d, J=6.82 Hz, 3 H) 0.85 (t, J=7.58 Hz, 3 H) 1.77-1.89 (m, 1 H) 1.94-2.06 (m, 1 H) 2.10-2.22 (m, 1 H) 2.23-2.36 (m, 1 H) 2.53-2.63 (m, 1 H) 2.64-2.74 (m, 1 H) 3.02 (dd, J=6.69, 2.91 Hz, 1 H) 3.16-3.26 (m, 1 H) 3.74 (s, 3 H) 3.80 (s, 3 H) 4.52 (s, 1 H) 5.94 (d, J=6.32 Hz, 2 H) 6.66 (s, 1 H) 6.79 (s, 1 H) 6.85 (d, J=8.59 Hz, 1 H) 6.96 (d, J=8.34 Hz, 1 H).

Example 24

9,10-Dimethoxy-8,8-dimethyl-13-pyridin-2-ylmethyl-5,8,13,13a-tetrahydro-6H-[1,3]dioxolo[4,5-g]isoquino[3,2-a]isoquinoline

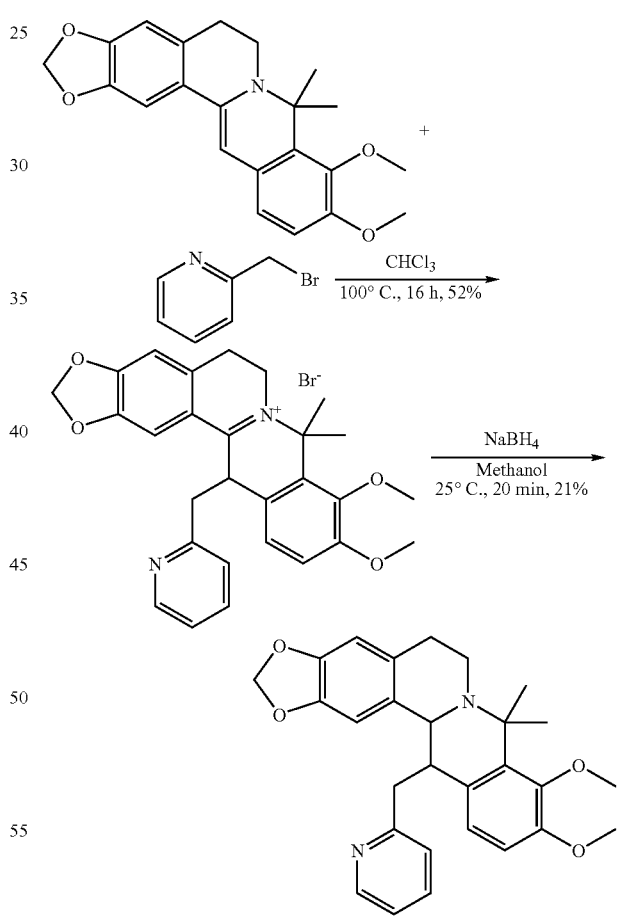

A mixture of 9,10-dimethoxy-8,8-dimethyl-5,8-dihydro-6H-[1,3]dioxolo[4,5-g]isoquino[3,2-a]isoquinoline (100 mg, 0.27 mmol) and 2-(bromomethyl)pyridine hydrobromide in chloroform was refluxed under nitrogen atmosphere for 16 h. The reaction mixture was cooled and the mixture was concentrated in vacuo. The residue was triturated with diethyl ether to afford 9,10-dimethoxy-8,8-dimethyl-13-pyridin-2- ylmethyl-5,6,8,13-tetrahydro-[1,3]dioxolo[4,5-g]isoquino[3,2-a]isoquinolin-7-ylium; bromide (79 mg, 52%). LC/MS m/e calcd for $C_{28}H_{29}BrN_2O_4$ (M+H)$^+$: 538.45, observed: 457.3; 1H NMR (400 MHz, MeOD) δ ppm 1.87 (s, 3 H) 1.99 (s, 3 H) 3.13-3.28 (m, 2H) 3.42-3.54 (m, 2 H) 3.71-3.84 (m, 1 H) 3.92 (s, 3 H) 3.98 (s, 3H) 4.58-4.68 (m, 1 H) 5.54 (t, J=6.82 Hz, 1 H) 6.19 (d, J=6.32 Hz, 2 H) 7.05 (t, J=4.29 Hz, 2 H) 7.17 (d, J=8.59 Hz, 1 H) 7.44 (d, J=7.83 Hz, 1 H) 7.64 (s, 1 H) 7.81 (t, J=6.69 Hz, 1 H) 8.22-8.31 (m, 1 H) 8.64 (d, J=5.31 Hz, 1 H).

To a solution of 9,10-dimethoxy-8,8-dimethyl-13-pyridin-2-ylmethyl-5,6,8,13-tetrahydro-[1,3]dioxolo[4,5-g]isoquino[3,2-a]isoquinolin-7-ylium; bromide (64 mg, 0.12 mmol) in methanol (10 mL) was added sodium borohydride (9 mg, 0.24 mmol) in small portions at 25° C. After stirring at 25° C. for 20 min, the mixture was concentrated in vacuo. The resulting residue was extracted with diethyl ether (2×50 mL), washed with water (2×25 mL), dried over anhydrous sodium sulfate and concentrated in vacuo to afford 9,10-dimethoxy-8,8-dimethyl-13-pyridin-2-ylmethyl-5,8,13,13a-tetrahydro-6H-[1,3]dioxolo[4,5-g]isoquino[3,2-a]isoquinoline (12 mg, 21%). LC/MS m/e calcd for $C_{28}H_{30}N_2O_4$ (M+H)$^+$: 459.56, observed: 459.3; 1H NMR (400 MHz, MeOD) δ ppm 1.87 (s, 3 H) 2.03 (s, 3 H) 3.00-3.09 (m, 2 H) 3.25-3.30 (m, 1 H) 3.55 (m, 1 H) 3.82 (s, 3 H) 3.89 (s, 3 H) 4.22 (t, J=5.68 Hz, 1 H) 4.26-4.33 (m, 1 H) 5.20 (d, J=5.05 Hz, 1 H) 6.01 (d, J=4.04 Hz, 2 H) 6.75 (s, 1 H) 6.98 (s, 1 H) 7.01-7.04 (m, 2 H) 7.18 (d, J=8.59 Hz, 1 H) 7.24-7.30 (m, 1 H) 7.73 (t, J=7.71 Hz, 1 H) 8.48 (d, J=5.05 Hz, 1 H).

Example 25

13-Benzyl-9,10-dimethoxy-8,8-dimethyl-5,8,13,13a-tetrahydro-6H-[1,3]dioxolo[4,5-g]isoquino[3,2-a]isoquinoline

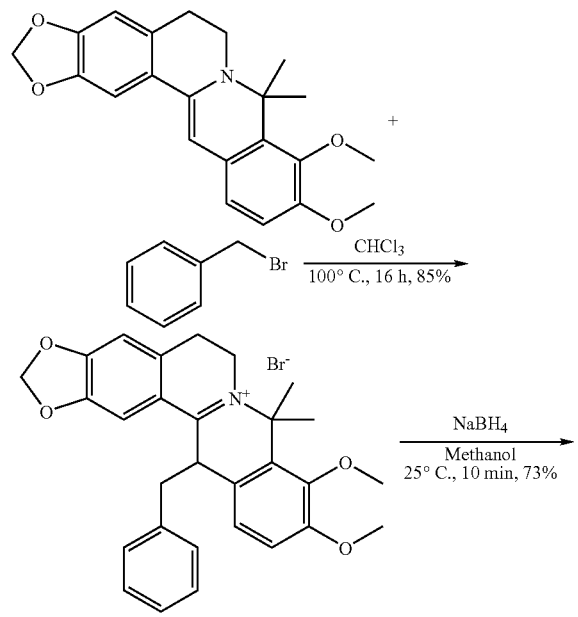

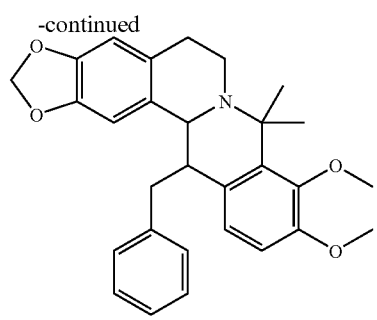

A mixture of 9,10-dimethoxy-8,8-dimethyl-5,8-dihydro-6H-[1,3]dioxolo[4,5-g]isoquino[3,2-a]isoquinoline (100 mg, 0.27 mmol) and benzyl bromide in chloroform was refluxed under nitrogen atmosphere for 16 h. The reaction mixture was cooled and concentrated in vacuo. The residue was triturated with diethyl ether to afford 13-benzyl-9,10-dimethoxy-8,8-dimethyl-5,6,8,13-tetrahydro-[1,3]dioxolo[4,5-g]isoquino[3,2-a]isoquinolin-7-ylium; bromide (124 mg, 85%). LC/MS m/e calcd for $C_{29}H_{30}BrNO_4$ (M+H)$^+$: 537.47, observed: 456.3; 1H NMR (400 MHz, DMSO-d6) δ ppm 0.82 (s, 3 H) 1.71 (s, 3 H) 2.63-2.78 (m, 1 H) 3.06-3.16 (m, 2 H) 3.16-3.25 (m, 1 H) 3.49-3.62 (m, 1 H) 3.79 (s, 3 H) 3.91 (s, 3 H) 4.33-4.44 (m, 1 H) 5.65 (s, 1 H) 6.17 (d, J=7.07 Hz, 2 H) 6.31 (d, J=8.84 Hz, 2 H) 7.08-7.19 (m, 3 H) 7.27 (s, 1 H) 7.31-7.39 (m, 2 H) 8.03 (s, 1 H).

To a solution of 13-benzyl-9,10-dimethoxy-8,8-dimethyl-5,6,8,13-tetrahydro-[1,3]dioxolo[4,5-g]isoquino[3,2-a]isoquinolin-7-ylium; bromide (100 mg, 0.19 mmol) in methanol (10 mL) was added sodium borohydride (14 mg, 0.38 mmol) in small portions at 25° C. After stirring at 25° C. for 10 min, the mixture was concentrated in vacuo. The resulting residue was extracted with diethyl ether (2×50 mL), washed with water (2×25 mL), dried over anhydrous sodium sulfate and concentrated in vacuo to afford 13-benzyl-9,10-dimethoxy-8,8-dimethyl-5,8,13,13a-tetrahydro-6H-[1,3]dioxolo[4,5-g]isoquino[3,2-a]isoquinoline (64 mg, 73%). LC/MS m/e calcd for $C_{29}H_{31}NO_4$ (M+H)$^+$: 458.57, observed: 458.3; 1H NMR (400 MHz, DMSO-d6) δ ppm 1.42 (s, 3 H) 1.64 (s, 3 H) 2.34-2.49 (m, 2 H) 2.53-2.68 (m, 2 H) 2.75-2.85 (m, 1 H) 3.11-3.16 (m, 1 H) 3.26-3.31 (m, 1 H) 3.72 (s, 3 H) 3.80 (s, 3 H) 4.14 (s, 1 H) 5.94-5.99 (m, 3 H) 6.64 (d, J=8.34 Hz, 1 H) 6.69 (s, 1 H) 6.76 (d, J=7.07 Hz, 2 H) 6.94 (s, 1 H) 7.06-7.17 (m, 3 H).

Example 26

9',10'-Dimethoxy-5',6',13',13a'-tetrahydrospiro[cyclopent-3-ene-1,8'-[1,3]dioxolo[4,5-g]isoquino[3,2-a]isoquinoline]

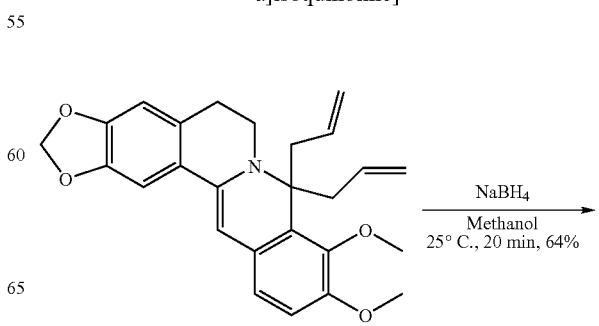

-continued

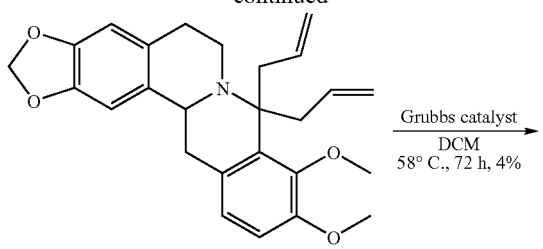

To a solution of 8,8-diallyl-9,10-dimethoxy-5,8-dihydro-6H-[1,3]dioxolo[4,5-g]isoquino[3,2-a]isoquinoline (110 mg, 0.26 mmol) in methanol (20 mL) was added sodium borohydride (10 mg, 0.26 mmol) in small portions at 25° C. After stirring at 25° C. for 20 min, the mixture was concentrated in vacuo. The resulting residue was extracted with diethyl ether (2×50 mL), washed with water (2×25 mL), dried over anhydrous sodium sulfate and concentrated in vacuo to afford 8,8-diallyl-9,10-dimethoxy-5,8,13,13a-tetrahydro-6H-[1,3]dioxolo[4,5-g]isoquino[3,2-a]isoquinoline (70 g, 64%). LC/MS m/e calcd for $C_{26}H_{29}NO_4$ (M+H)$^+$: 420.53, observed: 420.3; 1H NMR (400 MHz, DMSO-d6) δ ppm 2.32-2.44 (m, 2 H) 2.54-2.64 (m, 1 H) 2.64-2.75 (m, 3 H) 2.90 (s, 2 H) 3.02-3.12 (m, 2 H) 3.80 (d, J=2.78 Hz, 6 H) 4.30 (d, J=2.02 Hz, 1 H) 4.69 (d, J=10.36 Hz, 1 H) 4.74-4.88 (m, 2 H) 5.01 (d, J=16.93 Hz, 1 H) 5.36-5.48 (m, 1 H) 5.58-5.72 (m, 1 H) 5.93 (s, 2 H) 6.63 (s, 1 H) 6.78-6.85 (m, 2 H) 6.94 (d, J=8.59 Hz, 1 H).

To a solution of 8,8-diallyl-9,10-dimethoxy-5,8,13,13a-tetrahydro-6H-[1,3]dioxolo[4,5-g]isoquino[3,2-a]isoquinoline (68 mg, 0.16 mmol) in dry dichloromethane (50 mL) was added Grubbs' catalyst I (32 mg, 0.04 mmol) under nitrogen. The mixture was heated to reflux for 72 h at 58° C. The reaction mixture was cooled and concentrated in vacuo. Purification by Waters Automated Flash System (column: Xterra 30 mm×100 mm, sample manager 2767, pump 2525, detector: ZQ mass and UV 2487, solvent system: acetonitrile and 0.1% ammonium hydroxide in water) afforded 9',10'-dimethoxy-5',6',13',13a'-tetrahydrospiro[cyclopent-3-ene-1,8'-[1,3]dioxolo[4,5-g]isoquino[3,2-a]isoquinoline] (2.5 mg, 4%). LC/MS m/e calcd for $C_{24}H_{25}NO_4$ (M+H)$^+$: 392.47, observed: 392.3; 1H NMR (400 MHz, MeOD) δ ppm 2.34-2.43 (m, 2 H) 2.55-2.68 (m, 1 H) 2.68-2.75 (m, 1 H) 2.75-2.81 (m, 1 H) 2.85-2.92 (m, 1 H) 2.92-2.99 (m, 1 H) 3.03-3.10 (m, 1 H) 3.11 (d, J=3.03 Hz, 1 H) 3.14-3.18 (m, 1 H) 3.79 (s, 3 H) 3.84 (s, 3 H) 3.93-4.00 (m, 1 H) 5.78-5.83 (m, 1 H) 5.83-5.88 (m, 1 H) 5.90 (s, 2 H) 6.58 (s, 1 H) 6.78 (s, 1 H) 6.83 (s, 1 H) 6.91 (m, 1 H).

Example 27

9,10-Dimethoxy-8,8-dimethyl-5,8-dihydro-6H-[1,3]dioxolo[4,5-g]isoquino[3,2-a]isoquinoline

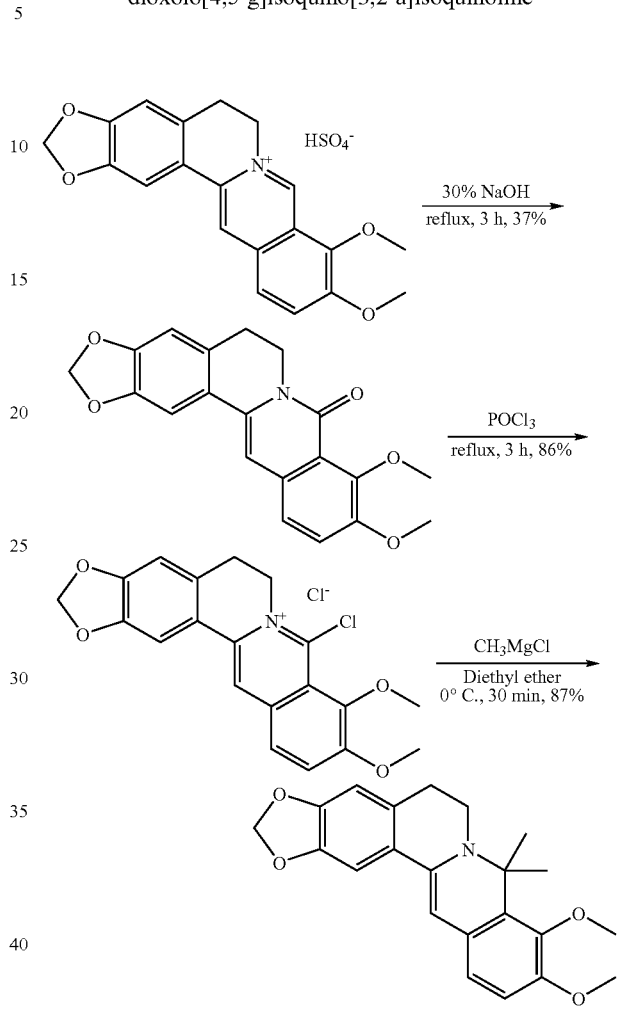

Berberine hydrogensulfate (10 g, 22.6 mmol) was dissolved in 30% sodium hydroxide in water (400 mL). The resulting mixture was refluxed for 3 h. The precipitate was collected and treated with hot 3% hydrochloric acid. The precipitate was collected and re-crystallized from ethanol to afford 9,10-dimethoxy-5,6-dihydro-6H-[1,3]dioxolo[4,5-g]isoquino[3,2-a]isoquinolin-8-one (3 g. 37%); LC/MS m/e calcd for $C_{20}H_{17}NO_5$ (M+H)$^+$: 352.36, observed: 352.0; 1H NMR (400 MHz, DMSO-d6) δ ppm 2.88 (t, J=6.06 Hz, 2 H) 3.78 (s, 3 H) 3.87 (s, 3 H) 4.12 (t, J=6.06 Hz, 2 H) 6.08 (s, 2 H) 6.93 (s, 1 H) 7.11 (s, 1 H) 7.41 (d, J=8.84 Hz, 1 H) 7.49 (s, 1 H) 7.53 (d, J=8.84 Hz, 1 H).

A mixture of 9,10-dimethoxy-5,6-dihydro-6H-[1,3]dioxolo[4,5-g]isoquino[3,2-a]isoquinolin-8-one (2 g, 5.7 mmol) and phosphorus oxychloride (20 mL) was refluxed for 4 h. After cooling, the orange-red crystalline residue was collected, washed with chloroform and dried in vacuo to afford 8-chloro-9,10-dimethoxy-5,6-dihydro-[1,3]dioxolo[4,5-g]isoquino[3,2-a]isoquinolin-7-ylium; chloride (2 g, 86%) as a solid which was used without further purification. LC/MS m/e calcd for $C_{20}H_{17}Cl_2NO_4$ (M+H)$^+$: 407.27.

To a suspension of 8-chloro-9,10-dimethoxy-5,6-dihydro-[1,3]dioxolo[4,5-g]isoquino[3,2-a]isoquinolin-7-ylium; chloride (2 g, 5 mmol) in anhydrous diethyl ether (150 mL) at 0° C. was added a solution of methylmagnesium chloride in tetrahydrofuran (3 M, 18 mL, 54 mmol) dropwise. After stirring at 0° C. for 30 min, the reaction was quenched by adding saturated aqueous ammonium chloride solution (50 mL). The mixture was extracted with diethyl ether (2×100 mL), washed with brine, dried over anhydrous sodium sulfate and concentrated in vacuo. The residue was re-crystallized from diethyl ether to afford 9,10-dimethoxy-8,8-dimethyl-5,8-dihydro-6H-[1,3]dioxolo[4,5-g]isoquino[3,2-a]isoquinoline (1.6 g, 87%). LC/MS m/e calcd for $C_{22}H_{23}NO_4$ (M+H)$^+$: 366.43, observed: 366.0; 1H NMR (400 MHz, DMSO-d6) δ ppm 1.65 (s, 6 H) 2.73 (t, J=5.56 Hz, 2 H) 3.27 (t, J=5.56 Hz, 2 H) 3.76 (s, 6H) 5.69 (s, 1 H) 5.99 (s, 2 H) 6.59 (d, J=8.34 Hz, 1 H) 6.74 (s, 1 H) 6.81 (d, J=8.34 Hz, 1 H) 7.21 (s, 1 H).

Example 28

8,8-Diethyl 9,10-dimethoxy-5,8-dihydro-6H-[1,3]dioxolo[4,5-g]isoquino[3,2-a]isoquinoline

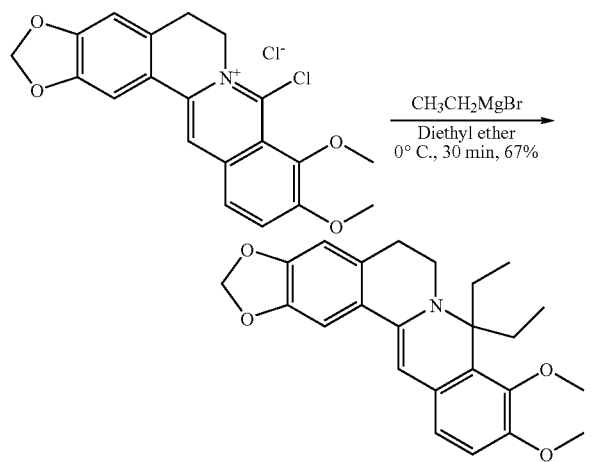

To a suspension of 8-chloro-9,10-dimethoxy-5,6-dihydro-[1,3]dioxolo[4,5-g]isoquino[3,2-a]isoquinolin-7-ylium; chloride (0.5 g, 1.2 mmol) in anhydrous diethyl ether (50 mL) at 0° C. was added a solution of ethylmagnesium bromide in tetrahydrofuran (3 M, 4.4 mL, 13 mmol) dropwise. After stirring at 0° C. for 30 min, the reaction was quenched by adding saturated aqueous ammonium chloride solution (30 mL). The mixture was extracted with diethyl ether (2×100 mL), washed with brine, dried over anhydrous sodium sulfate and concentrated in vacuo. The residue was re-crystallized from diethyl ether to afford 8,8-diethyl 9,10-dimethoxy-5,8-dihydro-6H-[1,3]dioxolo[4,5-g]isoquino[3,2-a]isoquinoline (320 mg, 67%). LC/MS m/e calcd for $C_{24}H_{27}NO_4$ (M+H)$^+$: 394.49, observed: 394.1; 1H NMR (400 MHz, DMSO-d6) δ ppm 0.79 (t, J=6.32 Hz, 6H) 1.78-1.95 (m, 2 H) 2.02-2.18 (m, 2 H) 2.73 (s, 2 H) 3.19 (s, 2 H) 3.74 (d, J=12.88 Hz, 6 H) 5.34 (s, 1 H) 5.99 (s, 2 H) 6.52 (d, J=8.34 Hz, 1 H) 6.74 (s, 1 H) 6.79 (d, J=8.08 Hz, 1 H) 7.18 (s, 1 H).

Example 29

Effectiveness in Muscular Glucose Utilization

L6 myoblasts were cultured in DMEM supplemented with 10% FBS. Confluent cells were differentiated to myotubes by culturing with DMEM supplemented with 2% FBS for 6 days. L6 myotubes were treated with compounds for 2 hours. Glucose uptake was performed in 16 h serum-starved cells. Cells were washed with PBS and incubated in Krebs-Ringer phosphate-HEPES buffer containing 0.1% BSA with or without 100 nmol/l insulin. Then, cells were incubated with 0.05 mmol/l 2-deoxy-D-glucose and 0.5 μCi 2-deoxy-D-[1,2-$^3$H] glucose for 10 min. The assay was terminated by washing the cells three times with ice-cold PBS. Cells were solubilised with 0.1% triton X-100 and radioactivity was determined by liquid scintillation counting. Total cellular protein concentration was measured by the Bradford method. Glucose uptake was performed in duplicate. The compounds were tested at concentrations of 1 uM and 3 uM. In this test, the compounds of formula (I) induce a glucose uptake activity between 1 and 2 fold the glucose uptake activity of the vehicle. Some particularly preferred compounds of formula (I) induce a glucose uptake activity between 1.2 and 2 fold the glucose uptake of the vehicle. Other particularly preferred compounds of formula (I) induce a glucose uptake activity between 1.4 and 2 fold the glucose uptake activity of the vehicle. Results are shown in table 1.

TABLE 1

| Example | Glucose uptake at 1 uM | Glucose uptake at 3 uM |
|---|---|---|
| 1 | 1.32 fold of vehicle | 1.30 fold of vehicle |
| 2 | 1.11 fold of vehicle | 1.07 fold of vehicle |
| 3 | 1.16 fold of vehicle | 1.11 fold of vehicle |
| 4 | 1.86 fold of vehicle | 1.46 fold of vehicle |
| 5 | | 1.15 fold of vehicle |
| 6 | | 1.07 fold of vehicle |
| 7 | 1.58 fold of vehicle | 1.68 fold of vehicle |
| 8 | 1.20 fold of vehicle | 1.35 fold of vehicle |
| 9 | 1.63 fold of vehicle | 0.99 fold of vehicle |
| 10 | 1.05 fold of vehicle | 1.22 fold of vehicle |
| 11 | 1.15 fold of vehicle | |
| 12 | 1.59 fold of vehicle | 1.22 fold of vehicle |
| 13 | 0.94 fold of vehicle | 1.05 fold of vehicle |
| 14 | 1.21 fold of vehicle | 1.18 fold of vehicle |
| 15 | 1.22 fold of vehicle | 1.14 fold of vehicle |
| 16 | 1.25 fold of vehicle | 0.91 fold of vehicle |
| 17 | 1.34 fold of vehicle | 1.04 fold of vehicle |
| 18 | 1.19 fold of vehicle | 1.05 fold of vehicle |
| 19 | 1.25 fold of vehicle | 1.24 fold of vehicle |
| 20 | 1.20 fold of vehicle | 1.18 fold of vehicle |
| 21 | 1.22 fold of vehicle | 1.14 fold of vehicle |
| 22 | 1.38 fold of vehicle | 1.46 fold of vehicle |
| 23 | 1.10 fold of vehicle | 1.14 fold of vehicle |
| 24 | 1.11 fold of vehicle | 1.03 fold of vehicle |
| 25 | 1.13 fold of vehicle | 1.02 fold of vehicle |
| 26 | 1.12 fold of vehicle | 1.11 fold of vehicle |
| 27 | 1.62 fold of vehicle | 1.65 fold of vehicle |
| 28 | 1.47 fold of vehicle | 1.12 fold of vehicle |

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I)

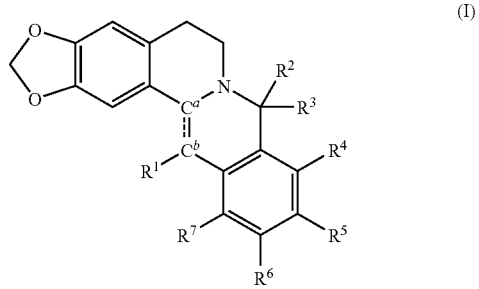

(I)

wherein
- $R^1$ is selected from the group consisting of: hydrogen, alkyl, alkenyl, phenylalkyl, pyridinylalkyl, alkylpyrazolylalkyl, carboxyalkyl, alkoxycarbonylalkyl, alkylaminocarbonylalkyl and oxetylaminocarbonylalkyl;
- $R^4$ is halogen or alkoxy;
- $R^5$ is halogen or alkoxy;
- $R^6$ is hydrogen or halogen;
- $R^7$ is hydrogen or halogen;

wherein $C^a$ and $C^b$ are each carbon atoms and the bond between $C^a$ and $C^b$ is a single bond or a double bond;
and wherein
- a) one of $R^2$ and $R^3$ is hydrogen and the other is selected from the group consisting of: phenyl, alkenyl and alkynyl;
- b) $R^2$ and $R^3$ are both at the same time alkyl, alkenyl or alkynyl; or
- c) $R^2$ and $R^3$, together with the carbon atom to which they are attached, form cycloalkyl, cycloalkenyl, oxetyl or tetrahydropyranyl;

or a pharmaceutically acceptable salt thereof;
with the proviso that 9,10-dimethoxy-8,8-dimethyl-5,8-dihydro-6H-[1,3]dioxolo[4,5-g]isoquino[3,2-a]isoquinoline; 8,8-diethyl-9,10-dimethoxy-5,8-dihydro-6H-[1,3]dioxolo[4,5-g]isoquino[3,2-a]isoquinoline; 8,8-diethyl-9,10-dimethoxy-5,8,13,13a-tetrahydro-6H-[1,3]dioxolo[4,5-g]isoquino[3,2-a]isoquinoline; 8-allyl-9,10-dimethoxy-5,8,13,13a-tetrahydro-6H-[1,3]dioxolo[4,5-g]isoquino[3,2-a]isoquinoline; 8-allyl-9,10-dimethoxy-5,8-dihydro-6H-[1,3]dioxolo[4,5-g]isoquino[3,2-a]isoquinoline; 9,10-dimethoxy-8-pent-4-enyl-5,8-dihydro-6H-[1,3]dioxolo[4,5-g]isoquino[3,2-a]isoquinoline; 9,10-dimethoxy-8-phenyl-5,8-dihydro-6H-[1,3]dioxolo[4,5-g]isoquino[3,2-a]isoquinoline; and 9,10-dimethoxy-8,8-dimethyl-5,8,13,13a-tetrahydro-6H-[1,3]dioxolo[4,5-g]isoquino[3,2-a]isoquinoline are excluded.

2. A compound according to claim 1, wherein $R^1$ is selected from the group consisting of: hydrogen, alkyl, alkenyl, phenylalkyl and pyridinylalkyl.

3. A compound according to claim 1, wherein $R^1$ is selected from the group consisting of: hydrogen, methyl, ethyl, propenyl, benzyl and pyridinylmethyl.

4. A compound according to claim 1, wherein $R^1$ is selected from the group consisting of: hydrogen, methyl and ethyl.

5. A compound according to claim 1, wherein one of $R^2$ and $R^3$ is hydrogen and the other is selected from the group consisting of: phenyl, ethenyl, propenyl, ethynyl and propynyl.

6. A compound according to claim 1, wherein one of $R^2$ and $R^3$ is hydrogen and the other is selected from the group consisting of propenyl, ethynyl and propynyl.

7. A compound according to claim 1, wherein $R^2$ and $R^3$ are both methyl at the same time, both ethyl at the same time or both propenyl at the same time.

8. A compound according to claim 1, wherein $R^2$ and $R^3$, together with the carbon atom to which they are attached, form cycloalkyl or cycloalkenyl.

9. A compound according to claim 1, wherein in c) $R^2$ and $R^3$, together with the carbon atom to which they are attached, form cyclopentyl or cyclopentenyl.

10. A compound according to claim 1, wherein $R^4$ is alkoxy.

11. A compound according to claim 1, wherein $R^4$ is methoxy.

12. A compound according to claim 1, wherein $R^5$ is alkoxy.

13. A compound according to claim 1, wherein $R^5$ is methoxy.

14. A compound according to claim 1, wherein $R^6$ is hydrogen.

15. A compound according to claim 1, wherein $R^7$ is hydrogen or chloro.

16. A compound according to claim 1 selected from the group consisting of:
- 9,10-Dimethoxy-8-vinyl-5,8-dihydro-6H-[1,3]dioxolo[4,5-g]isoquino[3,2-a]isoquinoline;
- 9',10'-Dimethoxy-5',6',13',13a'-tetrahydrospiro[cyclopentane-1,8'-[1,3]dioxolo[4,5-g]isoquino[3,2-a]isoquinoline];
- 8-Isopropenyl-9,10-dimethoxy-5,8-dihydro-6H-[1,3]dioxolo[4,5-g]isoquino[3,2-a]isoquinoline;
- 8-Ethynyl-9,10-dimethoxy-5,8-dihydro-6H-[1,3]dioxolo[4,5-g]isoquino[3,2-a]isoquinoline;
- 9,10-Dimethoxy-8-prop-1-ynyl-5,8-dihydro-6H-[1,3]dioxolo[4,5-g]isoquino[3,2-a]isoquinoline;
- 8-Isopropenyl-9,10-dimethoxy-13-methyl-5,8-dihydro-6H-[1,3]dioxolo[4,5-g]isoquino[3,2-a]isoquinoline;
- 9,10-Dimethoxy-13-methyl-8-prop-1-ynyl-5,8-dihydro-6H-[1,3]dioxolo[4,5-g]isoquino[3,2-a]isoquinoline;
- 13-Ethyl-8-isopropenyl-9,10-dimethoxy-5,8-dihydro-6H-[1,3]dioxolo[4,5-g]isoquino[3,2-a]isoquinoline;
- 8-Allyl-13-ethyl-9,10-dimethoxy-5,8-dihydro-6H-[1,3]dioxolo[4,5-g]isoquino[3,2-a]isoquinoline;
- 13-Ethyl-9,10-dimethoxy-8-prop-1-ynyl-5,8-dihydro-6H-[1,3]dioxolo[4,5-g]isoquino[3,2-a]isoquinoline;
- 13-Allyl-8-isopropenyl-9,10-dimethoxy-5,8-dihydro-6H-[1,3]dioxolo[4,5-g]isoquino[3,2-a]isoquinoline;
- 9,10-Dimethoxy-8,8,13-trimethyl-5,8-dihydro-6H-[1,3]dioxolo[4,5-g]isoquino[3,2-a]isoquinoline;

8,8-Diethyl-9,10-dimethoxy-13-methyl-5,8-dihydro-6H-[1,3]dioxolo[4,5-g]isoquino[3,2-a]isoquinoline;
13-Ethyl-9,10-dimethoxy-8,8-dimethyl-5,8-dihydro-6H-[1,3]dioxolo[4,5-g]isoquino[3,2-a]isoquinoline;
8,8-Diallyl-9,10-dimethoxy-5,8-dihydro-6H-[1,3]dioxolo[4,5-g]isoquino[3,2-a]isoquinoline;
13-Benzyl-9,10-dimethoxy-8,8-dimethyl-5,8-dihydro-6H-[1,3]dioxolo[4,5-g]isoquino[3,2-a]isoquinoline;
12-Chloro-9,10-dimethoxy-8,8-dimethyl-5,8-dihydro-6H-[1,3]dioxolo[4,5-g]isoquino[3,2-a]isoquinoline;
9',10'-Dimethoxy-5',6'-dihydrospiro[cyclopentane-1,8'-[1,3]dioxolo[4,5-g]isoquino[3,2-a]isoquinoline];
9,10-Dimethoxy-8,8,13-trimethyl-5,8,13,13a-tetrahydro-6H-[1,3]dioxolo[4,5-g]isoquino[3,2-a]isoquinoline;
8,8-Diethyl-9,10-dimethoxy-13-methyl-5,8,13,13a-tetrahydro-6H-[1,3]dioxolo[4,5-g]isoquino[3,2-a]isoquinoline;
9,10-Dimethoxy-8,8-dimethyl-13-pyridin-2-ylmethyl-5,8,13,13a-tetrahydro-6H-[1,3]dioxolo[4,5-g]isoquino[3,2-a]isoquinoline;
13-Benzyl-9,10-dimethoxy-8,8-dimethyl-5,8,13,13a-tetrahydro-6H-[1,3]dioxolo[4,5-g]isoquino[3,2-a]isoquinoline; and
9',10'-Dimethoxy-5',6',13',13a'-tetrahydrospiro[cyclopent-3-ene-1,8'-[1,3]dioxolo[4,5-g]isoquino[3,2-a]isoquinoline].

17. A compound according to claim 1 selected from the group consisting of:

9',10'-Dimethoxy-5',6',13',13a'-tetrahydrospiro[cyclopentane-1,8'-[1,3]dioxolo[4,5-g]isoquino[3,2-a]isoquinoline];
8-Isopropenyl-9,10-dimethoxy-5,8-dihydro-6H-[1,3]dioxolo[4,5-g]isoquino[3,2-a]isoquinoline;
8-Ethynyl-9,10-dimethoxy-5,8-dihydro-6H-[1,3]dioxolo[4,5-g]isoquino[3,2-a]isoquinoline;
9,10-Dimethoxy-8-prop-1-ynyl-5,8-dihydro-6H-[1,3]dioxolo[4,5-g]isoquino[3,2-a]isoquinoline;
8-Isopropenyl-9,10-dimethoxy-13-methyl-5,8-dihydro-6H-[1,3]dioxolo[4,5-g]isoquino[3,2-a]isoquinoline;
9,10-Dimethoxy-13-methyl-8-prop-1-ynyl-5,8-dihydro-6H-[1,3]dioxolo[4,5-g]isoquino[3,2-a]isoquinoline;
13-Ethyl-9,10-dimethoxy-8-prop-1-ynyl-5,8-dihydro-6H-[1,3]dioxolo[4,5-g]isoquino[3,2-a]isoquinoline;
9,10-Dimethoxy-8,8,13-trimethyl-5,8-dihydro-6H-[1,3]dioxolo[4,5-g]isoquino[3,2-a]isoquinoline;
12-Chloro-9,10-dimethoxy-8,8-dimethyl-5,8-dihydro-6H-[1,3]dioxolo[4,5-g]isoquino[3,2-a]isoquinoline;
9',10'-Dimethoxy-5',6'-dihydrospiro[cyclopentane-1,8'-[1,3]dioxolo[4,5-g]isoquino[3,2-a]isoquinoline];
9,10-Dimethoxy-8,8,13-trimethyl-5,8,13,13a-tetrahydro-6H-[1,3]dioxolo[4,5-g]isoquino[3,2-a]isoquinoline; and
9',10'-Dimethoxy-5',6',13',13a'-tetrahydrospiro[cyclopent-3-ene-1,8'-[1,3]dioxolo[4,5-g]isoquino[3,2-a]isoquinoline].

\* \* \* \* \*